(12) United States Patent
North et al.

(10) Patent No.: US 12,282,015 B2
(45) Date of Patent: Apr. 22, 2025

(54) SYSTEMS AND METHODS FOR TESTING AND SCREENING USING COMPOUND BOUND SUBSTRATES

(71) Applicant: Cerus Corporation, Concord, CA (US)

(72) Inventors: Anne North, Pleasant Hill, CA (US); Naheed Mufti, Concord, CA (US)

(73) Assignee: Cerus Corporation, Concord, CA (US)

( * ) Notice: Subject to any disclaimer, the term of this patent is extended or adjusted under 35 U.S.C. 154(b) by 0 days.

(21) Appl. No.: 18/243,045

(22) Filed: Sep. 6, 2023

(65) Prior Publication Data

US 2023/0408490 A1 Dec. 21, 2023

Related U.S. Application Data

(62) Division of application No. 16/472,813, filed as application No. PCT/US2017/068352 on Dec. 22, 2017, now abandoned.

(60) Provisional application No. 62/438,909, filed on Dec. 23, 2016.

(51) Int. Cl.
 *G01N 33/50* (2006.01)
 *G01N 33/555* (2006.01)

(52) U.S. Cl.
 CPC ......... *G01N 33/502* (2013.01); *G01N 33/555* (2013.01)

(58) Field of Classification Search
 CPC ..................... G01N 33/502; G01N 33/555
 See application file for complete search history.

(56) References Cited

U.S. PATENT DOCUMENTS

| | | | |
|---|---|---|---|
| 5,288,605 A | 2/1994 | Lin et al. | |
| 5,399,719 A | 3/1995 | Wollowitz et al. | |
| 5,459,030 A | 10/1995 | Lin et al. | |
| 5,482,828 A | 1/1996 | Lin et al. | |
| 5,556,993 A | 9/1996 | Wollowitz | |
| 5,559,250 A | 9/1996 | Cook | |
| 5,578,736 A | 11/1996 | Wollowitz | |
| 5,585,503 A | 12/1996 | Wollowitz | |
| 5,593,823 A | 1/1997 | Wolowitz et al. | |
| 5,618,662 A | 4/1997 | Lin et al. | |
| 5,625,079 A | 4/1997 | Wollowitz | |
| 5,654,443 A | 8/1997 | Wollowitz | |
| 5,691,132 A | 11/1997 | Wollowitz et al. | |
| 5,709,991 A | 1/1998 | Lin | |
| 5,712,085 A | 1/1998 | Wollowitz | |
| 5,871,900 A | 2/1999 | Wollowitz | |
| 5,908,742 A | 6/1999 | Lin et al. | |
| 5,965,349 A | 10/1999 | Lin | |
| 5,972,593 A | 10/1999 | Wollowitz | |
| 6,004,741 A | 12/1999 | Wollowitz | |
| 6,004,742 A | 12/1999 | Wollowitz | |
| 6,017,691 A | 1/2000 | Wollowitz et al. | |
| 6,093,725 A | 7/2000 | Cook et al. | |
| 6,133,460 A | 10/2000 | Wollowitz | |
| 6,143,490 A * | 11/2000 | Cook | A61K 35/16 435/238 |
| 6,171,777 B1 | 1/2001 | Cook | |
| 6,177,441 B1 | 1/2001 | Cook et al. | |
| 6,194,139 B1 | 2/2001 | Wollowitz | |
| 6,218,100 B1 | 4/2001 | Wollowitz | |
| 6,251,580 B1 | 6/2001 | Lin | |
| 6,270,952 B1 | 8/2001 | Cook et al. | |
| 6,281,225 B1 | 8/2001 | Hearst et al. | |
| 6,410,219 B1 | 6/2002 | Cook et al. | |
| 6,420,570 B1 | 7/2002 | Wollowitz | |
| 6,433,343 B1 | 8/2002 | Cimino et al. | |
| 6,455,286 B1 | 9/2002 | Wollowitz | |
| 6,469,052 B2 | 10/2002 | Wollowitz | |
| 6,503,699 B1 | 1/2003 | Wollowitz et al. | |
| 6,514,987 B1 | 2/2003 | Cook et al. | |
| 6,544,727 B1 | 4/2003 | Hei | |
| 6,586,749 B2 | 7/2003 | Cimino | |
| 6,686,480 B2 | 2/2004 | Wollowitz | |
| 6,709,810 B2 | 3/2004 | Cook | |
| 6,949,753 B2 | 9/2005 | Cimino | |
| 6,951,713 B2 | 10/2005 | Hei et al. | |
| 7,037,642 B2 | 5/2006 | Hei et al. | |
| 7,293,985 B2 | 11/2007 | Cook | |
| 7,611,831 B2 | 11/2009 | Hei | |
| 7,655,392 B2 | 2/2010 | Stassinopoulos | |

(Continued)

FOREIGN PATENT DOCUMENTS

EP 0805354 A1 11/1997
JP 2006133136 A 5/2006

(Continued)

OTHER PUBLICATIONS

Anonymous (Jan. 1, 2015). "ISBT 2015 Presented At 25th Regional Congress of the International Society of Blood Transfusion," Retrieved from the Internet: URL:http://interceptbloodsystem.com/sites/default/files/content/events/abstractbookisbt-2015.pdf, retrieved on Mar. 1, 2018, pp. 5, 21-23.

Cancelas, J. A. et al. (Nov. 2011). "Stored Red Blood Cell Viability Is Maintained After Treatment With A Second-Generation S-303 Pathogen Inactivation Process," Transfusion 51:2367-2376.

European Office Action, mailed Feb. 21, 2022, for European Patent Application No. 17835973.3, 16 pages.

Final Office Action, mailed Apr. 25, 2023, for U.S. Appl. No. 16/472,813, filed Jun. 21, 2019, 16 pages.

Final Office Action, mailed Feb. 10, 2022, for U.S. Appl. No. 16/472,813, filed Jun. 21, 2019, 11 pages.

Geisen, C. et al. (2014). "Characterization of Preexisting Antibodies to S-303 Pathogen Inactivated Red Blood Cells (S-303-RBC) in 11719 Patient Sera," Transfus. Med. Hemother 41(suppl 1):2-108, Abstracts (INF-V12), p. 33.

(Continued)

*Primary Examiner* — Shafiqul Haq
*Assistant Examiner* — Nam P Nguyen
(74) *Attorney, Agent, or Firm* — MORRISON & FOERSTER LLP

(57) ABSTRACT

The present disclosure provides compositions, methods, kits and systems for detecting antibodies in a biological sample. In some embodiments, methods/systems are particularly useful for detecting antibodies in patients against pathogen-inactivating compound treated RBCs.

10 Claims, 6 Drawing Sheets

(56) References Cited

U.S. PATENT DOCUMENTS

| | | |
|---|---|---|
| 8,900,805 B2 | 12/2014 | Mufti et al. |
| 9,259,525 B2 | 2/2016 | Hei |
| 9,713,627 B2 | 7/2017 | Mufti |
| 10,357,516 B2 | 7/2019 | Mufti |
| 10,799,533 B2 | 10/2020 | Corash |
| 10,842,818 B2 | 11/2020 | Vermeij |
| 11,096,963 B2 | 8/2021 | Corash et al. |
| 2001/0009756 A1 | 7/2001 | Hei |
| 2001/0018179 A1 | 8/2001 | Hei |
| 2002/0006393 A1 | 1/2002 | Wollowitz |
| 2002/0028432 A1 | 3/2002 | Cook |
| 2002/0042043 A1 | 4/2002 | Stassinopoulos |
| 2002/0115585 A1 | 8/2002 | Hei |
| 2002/0192632 A1 | 12/2002 | Hei |
| 2003/0062483 A1 | 4/2003 | Cimino |
| 2003/0105339 A1 | 6/2003 | Wollowitz |
| 2003/0113704 A1 | 6/2003 | Stassinopoulos |
| 2003/0207247 A1 | 11/2003 | Stassinopoulos |
| 2004/0021809 A1 | 2/2004 | Sumiyoshi et al. |
| 2004/0029897 A1 | 2/2004 | Cook |
| 2004/0180321 A1 | 9/2004 | Cook |
| 2004/0185544 A9 | 9/2004 | Hei |
| 2004/0185553 A9 | 9/2004 | Hei |
| 2004/0197343 A1 | 10/2004 | Dubensky et al. |
| 2004/0228877 A1 | 11/2004 | Dubensky et al. |
| 2005/0142542 A1 | 6/2005 | Hei |
| 2005/0175625 A1 | 8/2005 | Jaffee et al. |
| 2005/0215464 A1 | 9/2005 | Melnik et al. |
| 2005/0249748 A1 | 11/2005 | Dubensky et al. |
| 2005/0281783 A1 | 12/2005 | Kinch et al. |
| 2006/0093999 A1 | 5/2006 | Hei |
| 2006/0115466 A1 | 6/2006 | Stassinopoulos |
| 2007/0031457 A1 | 2/2007 | Dubensky et al. |
| 2007/0190029 A1 | 8/2007 | Pardoll et al. |
| 2007/0190063 A1 | 8/2007 | Bahjat et al. |
| 2007/0207170 A1 | 9/2007 | Dubensky et al. |
| 2007/0207171 A1 | 9/2007 | Dubensky et al. |
| 2010/0133160 A1 | 6/2010 | Hei |
| 2011/0286987 A1 | 11/2011 | Mufti |
| 2015/0157665 A1 | 6/2015 | Mufti |
| 2016/0354533 A1 | 12/2016 | Hei |
| 2017/0027986 A1 | 2/2017 | Corash et al. |
| 2017/0202882 A1 | 7/2017 | Vermeij |
| 2017/0304363 A1 | 10/2017 | Corash |
| 2018/0008639 A1 | 1/2018 | Mufti |
| 2018/0185484 A1 | 7/2018 | Greenman |
| 2018/0289873 A1 | 10/2018 | David |
| 2018/0318348 A1 | 11/2018 | Corash |
| 2019/0085289 A1 | 3/2019 | Greenman |
| 2019/0209718 A1 | 7/2019 | Church |
| 2019/0321407 A1 | 10/2019 | Erickson |
| 2019/0369087 A1 | 12/2019 | North et al. |
| 2020/0078406 A1 | 3/2020 | Weiner et al. |
| 2020/0397931 A1 | 12/2020 | Church et al. |
| 2020/0397935 A1 | 12/2020 | Church et al. |
| 2020/0405891 A1 | 12/2020 | Church et al. |
| 2021/0187020 A1 | 6/2021 | Corash et al. |
| 2021/0260114 A1 | 8/2021 | Corash et al. |
| 2021/0322479 A1 | 10/2021 | Vermeij |
| 2022/0031917 A1 | 2/2022 | Cahyadi et al. |

FOREIGN PATENT DOCUMENTS

| | | |
|---|---|---|
| JP | 2013256537 A | 12/2013 |
| WO | 199317553 A1 | 9/1993 |
| WO | 199403054 A1 | 2/1994 |
| WO | 199427433 A1 | 12/1994 |
| WO | 199500141 A1 | 1/1995 |
| WO | 199512973 A1 | 5/1995 |
| WO | 199519705 A1 | 7/1995 |
| WO | 199614737 A1 | 5/1996 |
| WO | 199614739 A1 | 5/1996 |
| WO | 199614740 A1 | 5/1996 |
| WO | 199639818 A1 | 12/1996 |
| WO | 199721346 A1 | 6/1997 |
| WO | 199830327 A1 | 7/1998 |
| WO | 199830545 A1 | 7/1998 |
| WO | 199903976 A2 | 1/1999 |
| WO | 199903976 A3 | 5/1999 |
| WO | 199926476 A1 | 6/1999 |
| WO | 199934839 A1 | 7/1999 |
| WO | 199934914 A1 | 7/1999 |
| WO | 199934915 A1 | 7/1999 |
| WO | 199963981 A2 | 12/1999 |
| WO | 200191775 A2 | 12/2001 |
| WO | 200191775 A3 | 6/2002 |
| WO | 200347650 A2 | 6/2003 |
| WO | 200361379 A2 | 7/2003 |
| WO | 200365787 A2 | 8/2003 |
| WO | 200361379 A3 | 10/2003 |
| WO | 200365787 A3 | 12/2003 |
| WO | 200347650 A3 | 2/2004 |
| WO | 2004049914 A2 | 6/2004 |
| WO | 2004050029 A2 | 6/2004 |
| WO | 2004050848 A2 | 6/2004 |
| WO | 2004050897 A2 | 6/2004 |
| WO | 2004050897 A3 | 8/2004 |
| WO | 2004050029 A3 | 10/2004 |
| WO | 2004084936 A2 | 10/2004 |
| WO | 2004050848 A3 | 12/2004 |
| WO | 2004110481 A2 | 12/2004 |
| WO | 2004049914 A3 | 2/2005 |
| WO | 2005009463 A2 | 2/2005 |
| WO | 2004110481 A3 | 3/2005 |
| WO | 2005037233 A2 | 4/2005 |
| WO | 2004084936 A3 | 6/2005 |
| WO | 2005009463 A3 | 6/2005 |
| WO | 2005067460 A2 | 7/2005 |
| WO | 2005071088 A2 | 8/2005 |
| WO | 2005092372 A2 | 10/2005 |
| WO | 2005071088 A3 | 11/2005 |
| WO | 2005037233 A3 | 1/2006 |
| WO | 2006050328 A1 | 5/2006 |
| WO | 2005092372 A3 | 6/2006 |
| WO | 2005067460 A3 | 10/2006 |
| WO | 2007022511 A2 | 2/2007 |
| WO | 2007022520 A2 | 2/2007 |
| WO | 2007022520 A3 | 5/2007 |
| WO | 2007022511 A3 | 9/2007 |
| WO | 2007103225 A2 | 9/2007 |
| WO | 2007103261 A2 | 9/2007 |
| WO | 2007117371 A2 | 10/2007 |
| WO | 2007103225 A3 | 5/2008 |
| WO | 2007103261 A3 | 12/2008 |
| WO | 2007117371 A3 | 12/2008 |
| WO | 2009126786 A2 | 10/2009 |
| WO | 2009126786 A3 | 7/2010 |
| WO | 2016014854 A1 | 1/2016 |
| WO | 2016057965 A1 | 4/2016 |
| WO | 2016115535 A1 | 7/2016 |
| WO | 2016210374 A1 | 12/2016 |
| WO | 2017070619 A1 | 4/2017 |
| WO | 2017120545 A2 | 7/2017 |
| WO | 2017120545 A3 | 8/2017 |
| WO | 2018125994 A1 | 7/2018 |
| WO | 2018161020 A1 | 9/2018 |
| WO | 2019060610 A1 | 3/2019 |
| WO | 2019133929 A1 | 7/2019 |
| WO | 2020061537 A1 | 3/2020 |
| WO | 2020263745 A1 | 12/2020 |
| WO | 2020263759 A2 | 12/2020 |
| WO | 2020264421 A1 | 12/2020 |
| WO | 2020263759 A3 | 1/2021 |

OTHER PUBLICATIONS

Geisen, C. et al. (Jul. 21, 2020). "Prevalence of Natural and Acquired Antibodies to Amustaline/Glutathione Pathogen Reduces Red Blood Cells," Transfusion 60(10):2389-2398.

Geisen, et al. (Jun. 1, 2013). "P-262: Screening Of Patients For Preexisting Antibodies To Pathogen Inactivated Red Blood Cells," Vox Sanguinis, Abstracts Of The 23rd Regional Congress Of The International Society Of Blood Transfusion, 105(Supp 1):156.

(56) References Cited

OTHER PUBLICATIONS

Henschler, R. et al. (Jan. 1, 2011). "Development of the S-303 Pathogen Inactivation Technology for Red Blood Cell Concentrates," Transfusion Medicine And Hemotherapy 38(1):33-42.

International Preliminary Report on Patentability, issued Jun. 25, 2019, for PCT Application No. PCT/US2017/068352, filed Dec. 22, 2017, 13 pages.

International Search Report and Written Opinion, mailed May 23, 2018, for PCT Application No. PCT/US2017/068352, filed Dec. 22, 2017, 22 pages.

Mufti, N.A et al. (Jan. 1, 2010). "Treatment of Whole Blood (WB) and Red Blood Cells (RBC) With S-303 Inactivates Pathogens and Retains in vitro Quality of Stored RBC," Biologicals 38(1):14-19.

Non-Final Office Action, mailed Jun. 1, 2021, for U.S. Appl. No. 16/472,813, filed Jun. 21, 2019, 9 pages.

Non-Final Office Action, mailed Oct. 5, 2022, for U.S. Appl. No. 16/472,813, filed Jun. 21, 2019, 13 pages.

North, A. et al. (Jan. 1, 2007)."P-309: Demonstration Of An S-303-Induced Immune Response In A Nave Rabbit Model Of Chronic Transfusion Using A Sensitive Flow Cytometry Assay," Vox Sanguinis 93(Supp. 1):168.

North, A. et al. (Oct. 2011). "Preclinical Pharmacokinetic and Toxicology Assessment Of Red Blood Cells Prepared With S-303 Pathogen Inactivation Treatment," Transfusion 51:2208-2218.

North, A.K. et al. (2010). "Evaluation of Naturally Occurring Antibodies to Pathogen Inactivated Red Blood Cells," 50 Suppl.:38A, Abstact, 1 page.

North, A.K. et al. (Jan. 1, 2006). "SP245: A Modified Process for Preparation of S-303 RBCs for Pathogen Inactivation Substantially Reduces Potential for Reactivity," Transfusion 46(9S):116A-117A.

Rios, J.A. et al. (Oct. 2006). "Viability Of Red Cells Prepared With S-303 Pathogen Inactivation Treatment," Transfusion 46:1778-1786.

Sapatneker, S. et al. (Mar. 1, 2015). "Molecular Typing for Red Blood Cell Antigens," Clinical Laboratory News, 5 pages.

U.S. Appl. No. 09/238,355, Greenman, W. et al., filed Jan. 27, 1999. (Copy not submitted herewith pursuant to the waiver of 37 C.F.R. § 1.98(a)(2)(iii) issued by the Office on Sep. 21, 2004.).

Benjamin, R. J. et al. (Nov. 1, 2005). "Therapeutic Efficacy and Safety of Red Blood Cells Treated with a Chemical Process (S-303) for Pathogen Inactivation: A Phase III Clinical Trial in Cardiac Surgery Patients," Transfusion 45(11):1739-1749.

Geisen, C. et al. (Jan. 1, 2014). "Abstract P-362: Screening of Patient Sera for Preexisting Antibodies to S-303 Pathogen Inactivated Red Blood Cells (S-303 RBC)," Vox Sanguinis 107:173, 1 page.

\* cited by examiner

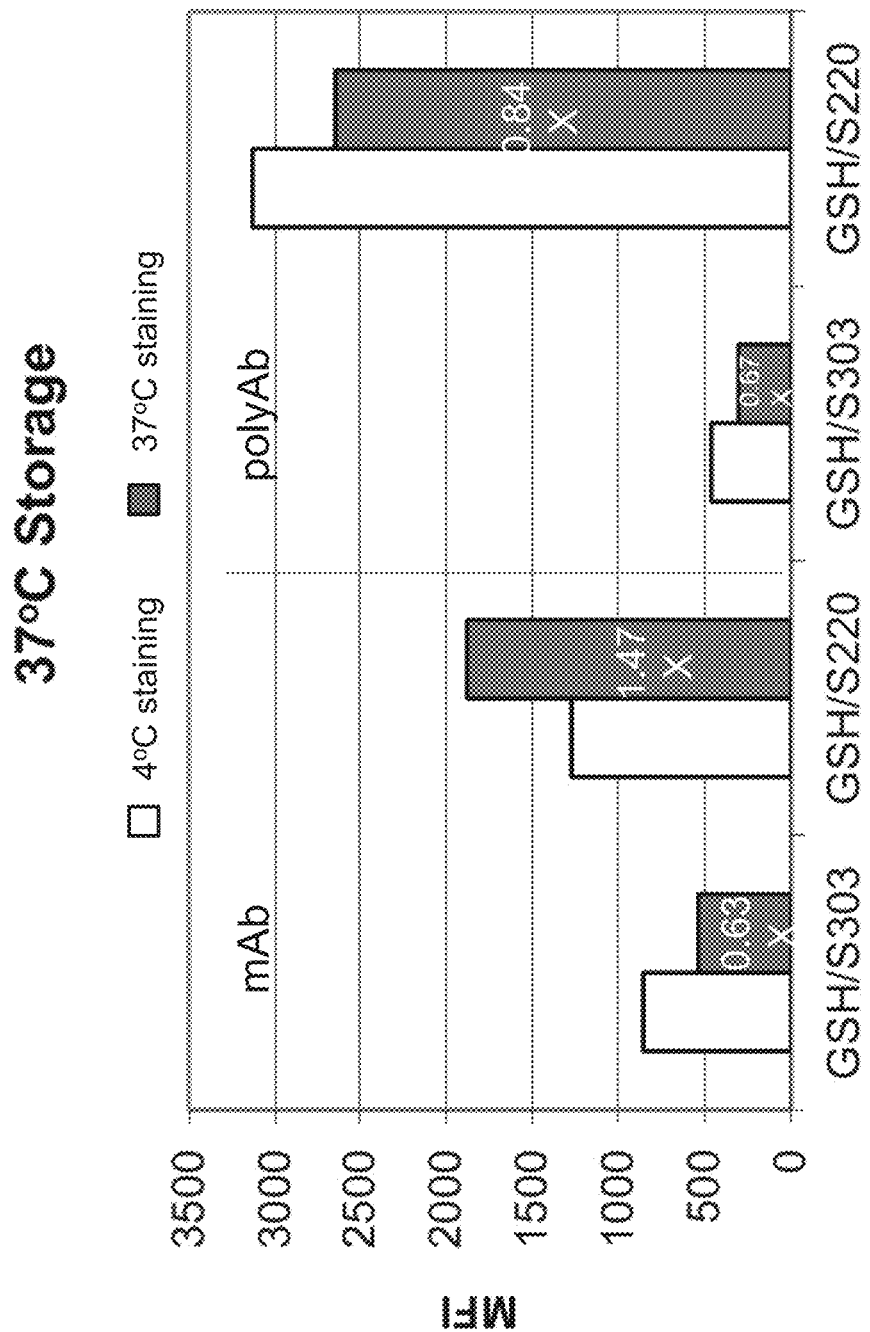

SYSTEMS AND METHODS FOR TESTING AND SCREENING USING COMPOUND BOUND SUBSTRATES

CROSS REFERENCE TO RELATED APPLICATION

This application is a divisional application of U.S. application Ser. No. 16/472,813, which adopts the international filing date of Dec. 22, 2017, which is a national stage application under 35 U.S.C. § 371 of International Application No. PCT/US2017/068352, filed internationally on Dec. 22, 2017, which claims the benefit of U.S. Provisional Application No. 62/438,909, filed on Dec. 23, 2016, the disclosures of which are hereby incorporated herein by reference in their entirety.

TECHNICAL FIELD

The present disclosure relates to systems and methods for testing and/or screening biological samples using compound bound substrates, such as reagent red blood cells.

BACKGROUND

The transfusion of blood or blood components is a commonly used medical practice. Blood products are generally tested for compatibility between a donor and recipient before a transfusion or utilization of the blood product in the recipient.

Blood group antigens are polymorphic protein or carbohydrate residues on red blood cells. These antigens can stimulate an antibody response in individuals who lack them, and some antibodies (e.g., clinically significant antibodies) can lead to hemolytic transfusion reaction or hemolytic disease. There are more than 300 blood group antigens (BGAs) on red blood cells, so transfusion recipients are often exposed to such antigens and immune responses to blood group antigens are observed for conventional red blood cell transfusions. Immune responses are more frequent in patents with multiple exposures to allogeneic red blood cells and/or certain conditions (e.g., SCD, thalassemia).

The detection of clinically significant blood group alloantibodies (cross match testing) is a critical test in pre-transfusion testing. Donors and patients are typically typed for ABO and Rh(D), as these are considered the most critical antigens for safe transfusion. Typing is generally not performed for minor antigens, such as those of the Rh (C/c and E/e), Kell (K/k), Duffy (Fya, Fyb), Kidd (Jka/Jkb), and MNS (M/N and S/s) systems, but plasma is screened for antibodies against these antigens. If a patient's antibody screen is negative, units for red blood cell (RBC) transfusion must also be ABO- and Rh(D)-compatible. If an antibody to a clinically significant minor antigen is present, units should additionally lack the corresponding antigen. Conventionally the antibody screen test has been carried out as either a solid-phase red cell adherence assay (e.g., Galileo System, Immucor) or an agglutination test in a test tube, such as for example, an antiglobulin test (e.g., direct antiglobulin test (DAT), indirect antiglobulin test (IAT)). This involves the use of human RBCs of known specificity, tested against plasma or serum samples. Following an incubation period, and most often addition of secondary antibody solutions, the mixture is viewed for hemagglutination. More recently this test has also been carried out using microplate and column agglutination technology systems known in the art, which can also be used with a degree of automation. However, the current test is limited in the range of clinically significant antibodies it can detect.

The transmission of disease by blood products and other biological materials remains a serious health problem. Nucleic acid targeting compounds, such as psoralens and psoralen derivatives for photochemical treatment with UVA light, have been introduced into blood products such as platelets and plasma to inactivate pathogens prior to transfusion and reduce the risk of transfusion-transmitted infection. Other nucleic acid targeting compounds, such as for example S-303 (e.g., amustaline), have been developed for pathogen inactivation treatment of RBCs. The S-303 compound forms covalent crosslinks with nucleic acids of contaminating pathogen and leukocytes to block replication and reduce the risk of transfusion-transmitted infection. However, a certain amount of these compounds or derivatives thereof have the potential to react with other nucleophiles in RBC components, including those on the surface of RBCs, which may in certain instances result in the compound or derivatives (e.g., moieties) thereof to become bound to RBCs, such as through the formation of surface bound adducts. Even where such pathogen-inactivated RBCs are generally considered to be safe and non-immunogenic, the compounds or derivatives thereof that are bound to the RBCs may in some instances be recognized by pre-existing antibodies or cause unwanted immune responses in certain patients.

Thus, there is a need for methods/systems to detect antibodies in patients against pathogen-inactivating compound treated RBCs.

SUMMARY

The compositions, methods, kits and systems of the present disclosure provide, among other uses, a means for detecting antibodies in a biological sample, such as for example to screen potential recipients of pathogen-inactivated RBCs for pre-existing cross-reactive antibodies prior to infusion of treated RBCs. In some embodiments, the compositions, methods, kits and systems are particularly useful for detecting antibodies in patients against S-303 compound treated RBCs.

In one aspect, provided is a kit, containing: (a) a first container that contains a first substrate, wherein a moiety is bound to the surface of the first substrate, and wherein the moiety is selected from the group consisting of compounds of any of Formulae I, II, III, IV, V, VI, VII, VIII, and IX, and derivatives thereof, or a salt or stereoisomer of any of the foregoing; and (b) a second container that contains a second substrate, wherein the surface of the second substrate lacks the bound moiety. In some embodiments, the moiety is selected from the group consisting of compounds of any of Formulae I, II, III, VII, VIII, and IX, and derivatives thereof, or a salt or stereoisomer of any of the foregoing. In some embodiments, the moiety is selected from the group consisting of compounds of any of Formulae IV, V, and VI, and derivatives thereof, or a salt or stereoisomer of any of the foregoing. In some embodiments, the moiety is selected from the group consisting of compounds of any of Formulae IV(a)-IV(h), and derivatives thereof, or a salt or stereoisomer of any of the foregoing. In some embodiments, the moiety is S-303, a derivative of S-303, or a salt of any of the foregoing. In some embodiments, the moiety is a non-frangible analog of S-303 or a salt thereof. In some embodiments, the moiety bound to the surface of the substrate is present at a loading level of at least about 10,000 moieties per substrate unit. In some embodiments, the moiety bound to the surface of the substrate is present at a loading level of at least about 50 moieties/$\mu m^2$. In some embodiments, the compound and the moiety bound to the surface are the same. In some embodiments, the compound and the moiety bound to the surface are different. In some embodiments, the first and the second substrates each comprise a polymeric particle, matrix, or portion of an assay plate. In some embodiments, the first substrate comprises red blood cells, wherein the second substrate comprises red blood cells, and wherein the red blood cells of the first and second substrates are obtained from one or more common donors. In some embodiments, the kit further contains a third container that contains a third substrate, wherein a first level of the moiety is bound to the surface of the first substrate, wherein a second level of the moiety is bound to the surface of the third substrate, and wherein the second level is less than the first level. In some embodiments, the first level of the moiety bound to the surface of the first substrate is at least 3-fold higher than the second level of the moiety bound to the surface of the third substrate. In some embodiments, the third substrate comprises a polymeric particle, matrix, or portion of an assay plate. In some embodiments, the third substrate comprises red blood cells, and wherein the red blood cells of the first, the second, and the third substrates are obtained from one or more common donors. In some embodiments, the first substrate comprises 2, 3, 4, 5, 6, 7, 8, 9, 10, or 11 samples, wherein each of the samples of the first substrate comprises red blood cells obtained from a different blood donor, and wherein the second substrate comprises a corresponding sample comprising red blood cells from each of the distinct blood donors. In some embodiments, the 2, 3, 4, 5, 6, 7, 8, 9, 10, or 11 samples represent multiple blood types. In some embodiments, the first substrate and the second substrate comprise red blood cells obtained from a donor of blood type O. In some embodiments, the first substrate, the second substrate and the third substrate comprise red blood cells obtained from a donor of blood type O. In some embodiments, the first substrate and the second substrate comprise red blood cells in a buffered suspension medium at about 0.5% to about 5% red blood cells. In some embodiments, the first substrate, the second and the third substrate comprise red blood cells in a buffered suspension of about 0.5% to about 5% red blood cells. In some embodiments, the first container that contains a first substrate, the second container that contains a second substrate, and/or the kit that contains the first container and the second container is suitable for storage at 2-8° C. In some embodiments, the first container that contains a first substrate, the second container that contains a second substrate, and/or the kit that contains the first container and the second container is suitable for storage at room temperature. In some embodiments, the first container that contains a first substrate, the second container that contains a second substrate, and/or the kit that contains the first container and the second container is suitable for storage at less than −20° C.

In another aspect, provided is a method of preparing a panel of substrates, the method comprising: a) providing a first and a second sample each comprising a substrate; and b) treating the substrate of the first sample with a compound, wherein treatment with the compound results in binding of a moiety to the surface of the substrate of the first sample; wherein the second sample is not treated with the compound, thereby producing a panel comprising a first sample of a substrate with a surface-bound moiety and a second sample of a substrate that lack the surface-bound moiety, and wherein the compound is selected from the group consisting of compounds of any of Formulae I, II, III, IV(a)-IV(h), VII, VIII, and IX, and derivatives thereof, or a salt or stereoisomer of any of the foregoing. In some embodiments, a method of preparing a panel of polymeric particles is provided, the method comprising: a) providing a first and a second sample comprising polymeric particles; and b) treating the polymeric particles of the first sample with a compound, wherein treatment with the compound results in binding of a moiety to the surface of particles of the first sample; wherein the second sample is not treated with the compound, thereby producing a panel comprising a first sample of polymeric particles with a surface-bound moiety and a second sample of polymeric particles that lack the surface-bound moiety, and wherein the compound is selected from the group consisting of compounds of any of Formulae I, II, III, IV(a)-IV(h), VII, VIII, and IX, and derivatives thereof, or a salt or stereoisomer of any of the foregoing. In some embodiments, a method of preparing a panel of red blood cells is provided, the method comprising: a) providing a first and a second sample comprising red blood cells; and b) treating the red blood cells of the first sample with a compound, wherein treatment with the compound results in binding of a moiety to the surface of red blood cells of the first sample; wherein the second sample is not treated with the compound, thereby producing a panel comprising a first sample of red blood cells with a surface-bound moiety and a second sample of red blood cells that lack the surface-bound moiety, and wherein the compound is selected from the group consisting of compounds of any of Formulae I, II, III, IV(a)-IV(h), VII, VIII, and IX, and derivatives thereof, or a salt or stereoisomer of any of the foregoing. In some embodiments, the compound is selected from the group consisting of compounds of any of Formulae I, II, III, VII, VIII, and IX, and derivatives thereof, or a salt or stereoisomer of any of the foregoing. In some embodiments, the compound is selected from the group consisting of compounds of any of Formulae IV(a)-IV(h), and derivatives thereof, or a salt or stereoisomer of any of the foregoing. In some embodiments, the compound is a derivative of S-303, or a salt thereof. In some embodiments, the compound is a non-frangible analog of S-303, or a salt thereof. In some embodiments, the surface-bound moiety is a derivative of S-303, or a salt thereof. In some embodiments, the surface-bound moiety is a non-frangible analog of S-303, or a salt thereof. In some embodiments, the moiety bound to the surface of the red blood cells is present at a loading level of at least about 10,000 moieties per red blood cell. In some embodiments, the moiety bound to the surface of the red blood cells is present at a loading level of at least about 50 moieties/$\mu m^2$. In some embodiments, the compound and the surface-bound moiety are the same. In some embodiments, the compound and the surface-bound moiety are different. In some embodiments, the red blood cells of the first and the second samples are obtained from the same blood donor. In some embodiments, the red blood cells of the first and the second samples are obtained from a donor of blood type O. In some embodiments, treating the substrate of the first sample with a compound, wherein treatment with the compound results in binding of a moiety to the surface of the substrate of the first sample, is performed at 2-8° C. In some embodiments, treating the substrate of the first sample with a compound, wherein treatment with the compound results in binding of a moiety to the surface of the substrate of the first sample, is performed at room temperature. In some embodiments, the method further comprises, after step (b): washing the first and the second samples. In some embodiments, the method further comprises, after step (b): resuspending the first and the second samples in a buffered suspension medium at about 0.5% to about 5% red blood cells. In some embodiments, the method further comprises, after step (b): adding a cryopreservative to the first and the second samples; and freezing the first and the second samples. In some embodiments, the method further comprises, after step (b), storing the first and second samples at refrigeration temperature (e.g., 2-8° C.). In some embodiments, the method comprises, after step (b), storing the first and second samples at less than about −20° C. In some embodiments, the method comprises, after step (b), storing the first and second samples at room temperature. In some embodiments, the method further comprises: treating a third sample comprising red blood cells with the compound, wherein treatment of the red blood cells of the third sample with the compound leads to a second level of the moiety bound to the surface of red blood cells of the third sample, wherein a first level of the moiety is bound to the surface of red blood cells of the first sample, and wherein the second level is less than the first level. In some embodiments, the method further comprises, after treating the third sample with the compound, washing the third sample. In some embodiments, the method further comprises, after treating the third sample with the compound: adding a cryopreservative to the third sample; and freezing the third sample. In some embodiments, the method further comprises, after treating the third sample with the compound: resuspending the third sample in a buffered suspension medium at about 0.5% to about 5% red blood cells. In some embodiments the method further comprises, after treating the third sample with the compound, storing the third sample at refrigeration temperature or at room temperature.

In another aspect, provided is a method of testing a sample for the presence of an antibody that binds a compound, the method comprising: a) providing a sample comprising serum or plasma; b) contacting the sample with a substrate, wherein a moiety is bound to the surface of the substrate; and wherein the moiety is selected from the group consisting of compounds of any of Formulae I, II, III, IV, IV(a)-IV(h), V, VI, VII, VIII, and IX, and derivatives thereof, or a salt or stereoisomer of any of the foregoing; and c) assaying an amount of binding between antibody from the sample and the surface-bound moiety of the substrate, wherein binding between the antibody and the surface-bound moiety indicates that the antibody binds the compound. In some embodiments, the method of testing a sample for the presence of an antibody that binds a compound comprises: a) providing a sample comprising serum or plasma; b) contacting the sample with a polymeric particle (e.g., bead, microsphere), matrix or portion of an assay plate, wherein a moiety is bound to the surface of the polymeric particle (e.g., bead, microsphere), matrix or portion of an assay plate; and wherein the moiety is selected from the group consisting of compounds of any of Formulae I, II, III, IV, IV(a)-IV(h), V, VI, VII, VIII, and IX, and derivatives thereof, or a salt or stereoisomer of any of the foregoing; c) assaying an amount of binding between antibody from the sample and the surface-bound moiety of the polymeric particle (e.g., bead, microsphere), matrix or portion of an assay plate, wherein binding between the antibody and the surface-bound moiety indicates that the antibody binds the compound. In some embodiments, the method of testing a sample for the presence of an antibody that binds a compound comprises: a) providing a sample comprising serum or plasma; b) contacting the sample with red blood cells, wherein a moiety is bound to the surface of the red blood cells; and wherein the moiety is selected from the group consisting of compounds of any of Formulae I, II, III, IV(a)-IV(h), VII, VIII, and IX, and derivatives thereof, or a salt or stereoisomer of any of the foregoing; and c) assaying an amount of binding between antibody from the sample and the surface-bound moiety of the red blood cells, wherein binding between the antibody and the surface-bound moiety indicates that the antibody binds the compound. In some embodiments, the compound is selected from the group consisting of compounds of any of Formulae I, II, III, VII, VIII, and IX, and derivatives thereof, or a salt or stereoisomer of any of the foregoing. In some embodiments, the compound is selected from the group consisting of compounds of any of Formulae IV(a)-IV(h), and derivatives thereof, or a salt or stereoisomer of any of the foregoing. In some embodiments, the compound is a derivative of S-303, or a salt thereof. In some embodiments, the compound is a non-frangible analog of S-303, or a salt thereof. In some embodiments, the surface-bound moiety is a derivative of S-303, or a salt thereof. In some embodiments, the surface-bound moiety is a non-frangible analog of S-303, or a salt thereof. In some embodiments, the moiety bound to the surface of the red blood cells is present at a loading level of at least about 10,000 moieties per red blood cell. In some embodiments, the moiety bound to the surface of the red blood cells is present at a loading level of at least about 50 moieties/µm$^2$. In some embodiments, the compound and the surface-bound moiety are the same. In some embodiments, the compound and the surface-bound moiety are different. In some embodiments, step (c) comprises comparing the amount of binding between antibody from the sample and the surface-bound moiety with a reference, and wherein an increased amount of binding as compared with the reference indicates the presence of the antibody in the sample. In some embodiments, step (c) comprises assaying an amount of binding between antibody from the sample and red blood cells that lack the surface-bound moiety. In some embodiments, step (c) further comprises assaying an amount of binding between antibody from the sample and red blood cells having a reduced amount of the surface-bound moiety. In some embodiments, step (b) comprises contacting the sample and the red blood cells with anti-human globulin, and wherein step (c) comprises assaying an amount of agglutination.

In another aspect, provided is a method of providing a red blood cell transfusion to a patient, wherein the red blood cell transfusion comprises red blood cells treated with a pathogen-inactivating compound, the method comprising: a) providing a sample comprising serum or plasma from the patient; b) contacting the sample with a first substrate, wherein a moiety is bound to the surface of the substrate; c) assaying an amount of binding between antibody from the sample and the surface-bound moiety of the first substrate as compared to a reference, wherein binding between the antibody and the surface-bound moiety indicates that the antibody binds red blood cells treated with the pathogen-inactivating compound; d) determining whether the amount of binding is higher than the reference; and f) in accordance with a determination that the amount of binding is not higher than the reference, providing the blood transfusion to the patient. In some embodiments, the surface-bound moiety is selected from the group consisting of compounds of any of Formulae I, II, III, IV, V, VI, VII, VIII, and IX, and derivatives thereof, or a salt or stereoisomer of any of the foregoing. In some embodiments, the surface-bound moiety is selected from the group consisting of compounds of any of Formulae I, II, III, VII, VIII, and IX, and derivatives thereof, or a salt or stereoisomer of any of the foregoing. In some embodiments, the surface-bound moiety is selected from the group consisting of compounds of any of Formulae IV, V, and VI, and derivatives thereof, or a salt or stereoisomer of any of the foregoing. In some embodiments, the surface-bound moiety is selected from the group consisting of compounds of any of Formulae IV(a)-IV(h), and derivatives thereof, or a salt or stereoisomer of any of the foregoing. In some embodiments, the surface-bound moiety is S-303, a derivative of S-303, or a salt of any of the foregoing. In some embodiments, the surface-bound moiety is a non-frangible analog of S-303 or a salt thereof. In some embodiments, the compound and the surface-bound moiety are the same. In some embodiments, the compound and the surface-bound moiety are different. In some embodiments, the first substrate comprises a polymeric particle, matrix, or portion of an assay plate. In some embodiments, the first substrate comprises red blood cells. In some embodiments, step (c) comprises assaying an amount of binding between antibody from the sample and a second substrate that lacks the surface-bound moiety. In some embodiments, the second substrate is the same as the first substrate. In some embodiments, step (c) further comprises assaying an amount of binding between antibody from the sample and third substrate having a lesser amount of the surface-bound moiety, as compared with the first substrate. In some embodiments, the third substrate is the same as the first substrate. In some embodiments, step (b) comprises contacting the sample and the substrate(s) with anti-human globulin, and wherein step (c) comprises assaying an amount of agglutination. In some embodiments, the moiety bound to the surface of the substrate(s) is not the same as the pathogen-inactivating compound.

In another aspect, provided is a composition comprising a human red blood cell, wherein a moiety selected from the group consisting of compounds of any of Formulae I, II, III, IV(a)-IV(h), VI, VII, VIII, and IX, and derivatives thereof, or a salt or stereoisomer of any of the foregoing is bound to the surface of the human red blood cell. In some embodiments, the moiety is selected from the group consisting of compounds of any of Formulae I, II, III, VII, VIII, and IX, and derivatives thereof, or a salt or stereoisomer of any of the foregoing. In some embodiments, the moiety is a non-frangible analog of S-303 or a salt thereof.

DESCRIPTION OF THE DRAWINGS

FIG. 6 is a graph showing levels of antibody staining of treated red blood cells.

DETAILED DESCRIPTION

Figure 1:
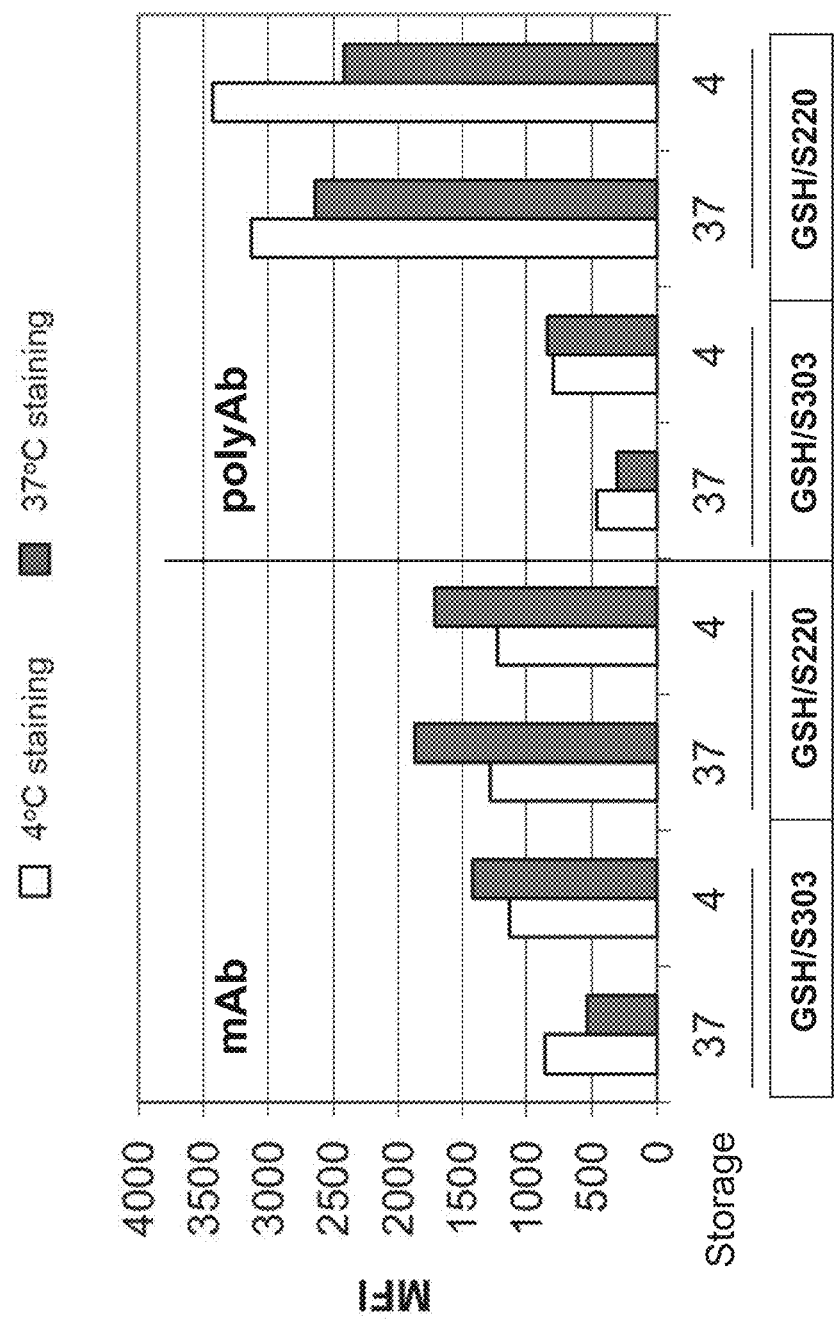
FIG. 1 is a graph showing levels of antibody staining of treated red blood cells.

The present disclosure provides methods and systems for testing and/or screening biological samples using a substrate having a compound bound thereon. We have found that while a compound (e.g., pathogen-inactivating compound) used in accordance with various embodiments of the present disclosure may be safe and effective for the treatment (e.g., pathogen inactivation) of red blood cells (RBCs), such treatment has the potential for the compound to react with other nucleophiles in the RBCs, which may in certain instances result in binding of the compound to RBCs, such as for example to the surface of RBCs (e.g., formation of surface bound adducts). Such binding may also result in antibodies specific for the compound or a portion thereof also binding to treated RBCs, if such antibodies are present in the patient infused with the treated RBCs. Thus, it is important to test a biological sample (e.g., sample from a patient) to evaluate for the presence or absence of antibodies (e.g., clinically significant antibodies) to the compound or portion thereof. The present application contemplates the methods/systems described herein and recognizes the use of those methods/systems in testing a biological sample for the presence of an antibody against the compound using compositions and/or kits comprising compounds of the present disclosure bound on substrates. In accordance with some embodiments, the methods/systems are particularly suitable for detecting pre-existing antibodies in patients, prior to transfusion, which react with pathogen-inactivating compound-treated RBCs.

Provided herein are compositions of compound-bound substrates (e.g., pathogen-inactivating compound-bound RBCs) and kits/systems, methods of preparing the compositions, and uses thereof.

The articles "a" and "an" are used herein to refer to one or to more than one (i.e., to at least one) of the grammatical object of the article. By way of example, "a substrate" means one substrate or more than one substrate.

"Biological sample," or simply "sample", as that term is used herein, means a sample, such as one that is, but need not be, obtained from an animal (e.g., human), which sample, or component thereof, can be used to assess the presence, absence and/or level, of an antibody according to the methods of the disclosure. Such sample includes, but is not limited to, any biological samples, such as for example a biological fluid (e.g., blood, serum, plasma, lymph, semen, sputum, saliva, phlegm, tears, and the like), and any sample obtained from an animal (e.g., human) that can be assayed for the presence or absence of an antibody.

"Alkyl" as used herein refers to a cyclic, branched, or straight chain chemical group containing carbon and hydrogen, such as methyl, pentyl, and adamantyl. Alkyl groups can be either unsubstituted or substituted with one or more substituents, e.g., halogen, alkoxy, acyloxy, amino, hydroxyl, thiol, carboxy, benzyloxy, phenyl, benzyl, or other functionality Alkyl groups can be saturated or unsaturated (e.g., containing —C=C— or —C—C— subunits), at one or several positions. Typically, alkyl groups will comprise 1 to 12 carbon atoms, such as 1 to 10 carbon atoms or 1 to 8 carbon atoms, unless otherwise specified.

"Heteroalkyl" as used herein refers to an alkyl chain with one or more N, O, S, or P heteroatoms incorporated into the chain. The heteroatom(s) may bear none, one, or more than one of the substituents descried above. "Heteroatoms" also includes oxidized forms of the heteroatoms N, S, and P. Examples of heteroalkyl groups include, without limitation, methoxy, ethoxy, and other alkoxy groups; ether-containing groups, amide-containing groups such as polypeptide chains; ring systems such as piperidinyl, lactam, and lactone; and other groups that incorporate heteroatoms into the carbon chain. Typically, heteroalkyl groups will comprise, in addition to the heteroatom(s), 1 to 12 carbon atoms, such as 1 to 10 carbon atoms or 1 to 8 carbon atoms, unless otherwise specified.

"Aryl" or "Ar" refers to an unsaturated aromatic carbocyclic group having a single ring (e.g., phenyl) or multiple condensed rings (e.g., naphthyl or anthryl), which are optionally unsubstituted or substituted with amino, hydroxyl, $C_{1-8}$ alkyl, alkoxy, halo, thiol, and other substituents.

"Heteroaryl" groups are unsaturated aromatic carbocyclic groups having a single ring (e.g., pyridyl or furyl) or multiple condensed rings (e.g., acridinyl, indolyl, or benzothienyl) and having at least one hetero atom, such as N, O, or S, within at least one of the rings. The ring(s) are optionally unsubstituted or substituted with amino, hydroxyl, alkyl, alkoxy, halo, thiol, acyloxy, carboxy, benzyloxy, phenyl, benzyl, and other substituents.

Compositions

Provided herein are compositions containing a substrate having a surface-bound moiety, wherein the surface-bound moiety is suitable for binding antibodies against a compound, such as for example, a compound used in the preparation of pathogen-inactivated red blood cells, that may be present in a biological sample.

Substrate

As will be appreciated by one of ordinary skill in the art, a substrate can be any solid support known in the art. The solid support may be composed of any material (e.g., biological, synthetic) or matrix suitable for binding the surface-bound moiety. Examples of solid supports include polymers or copolymers (e.g., polyesters, polyethers, polyolefins, polyamides, polysaccharides, polyurethanes, styrenes and styrene derivatives, polystyrenes, celluloses), plastic, glass, gold and other metals, etc. Additional examples of solid supports include cells (e.g., RBCs), cell membranes and other cell-derived material. A solid support can present the surface-bound moiety in a two-dimensional format (e.g., a plate) or a three-dimensional format (e.g., a cell, a particle, a bead or other spherical or quasi-spherical object). Additional examples of solid supports include particles (e.g., polymeric particles), such as for example, beads and microspheres (e.g., synthetic beads and microspheres, beads and microspheres of polymers or copolymers). Binders may also be used to give the solid supports integrity and structure. A substrate can be a portion of an assay plate. Particular solids supports are composed of one or more materials to which the biological sample will not bind or will not substantially bind. For instance, the solid support may be composed of a material to which antibodies do not bind or do not substantially bind (e.g., material not comprising antigen(s) to which particular antibodies bind). In particular, the solid support is composed of a material to which antibodies against pathogen-inactivated red blood cells do not bind or do not substantially bind.

Any solid support for use in the present compositions and methods may be suitable for covalent or non-covalent attachment for the surface-bound moiety. In some embodiments, the solid support is inert. In some embodiments, the surface-bound moiety can be covalently or non-covalently bound to the solid support material itself. In other embodiments, the solid support material is functionalized with a reactive group (e.g., amine (—$NH_2$) or ammonium (—$NH_3+$ or —$NR_3+$) functional group, alcoholic functional group (—OH), carboxylic functional group (—COOH) isocyanate functional group (—NCO)) that can interact with or otherwise covalently or non-covalently bind to the surface-bound moiety.

It may be advantageous for the substrate to be stable at a variety of different temperatures, such as room temperature, refrigeration temperature, or freezing temperatures. In some embodiments, the substrate is stable at room temperature. In some embodiments, the substrate is stable at refrigeration temperature (e.g., 1-6° C., 2-8° C., 2-4° C.). In some embodiments, the substrate is stable at 0° C. or less than 0° C. (e.g., −20° C.). In some embodiments, the substrate is stable at −80° C.

In accordance with certain embodiments of the present disclosure, a substrate comprises RBCs. For example, RBCs often used in immunohaematological tests can be a substrate as provided herein.

In some embodiments, RBCs are prepared from human blood. The substrate can include RBCs from any blood group, such as group 0, group A, group B, or group AB donors. RBCs may be specifically designed to support resolution of one or more antibody mixtures. In some embodiments, RBCs express antigens selected from the group consisting of antigens C, c, E, e, K, k, Fya, Fyb, Jka, Jkb, M, N, S, s, P1, Lea and Leb. In some embodiments, RBCs express Rh(D). In some embodiments, RBCs are of an Rh type selected from the group consisting of $R_1R_1$, $R_2R_2$, $R_1^wR_1$, $R_0r$, and rr. RBCs may be stored at room temperature (e.g., in a buffered suspension medium at 0.5%-5% RBCs), refrigeration temperature (e.g., in a buffered suspension medium at 0.5%-5% RBCs), or they may be frozen (e.g., in a cryopreservative such as for example, glycerolyte, and stored at −80° C.).

RBCs employed as substrates in the present compositions can be obtained from a single donor, or they may be obtained from two or more donors (e.g., a mixture of RBCs obtained from two or more donors). In some embodiments, the RBC substrate comprises RBC obtained from 2, 3, 4, 5, 6, 7, 8, 9, 10, or 11 or more individual donors. In some instances, the RBCs from the two or more donors have one or more property in common, such as ABO blood group or the presence or absence of other RBC antigens (e.g., common RBC antigens, clinically relevant RBC antigens). In other instances, the RBCs from the two or more donors are heterogeneous with respect to certain properties, such as ABO blood group or the presence or absence of other RBC antigens (e.g., common RBC antigens, clinically relevant RBC antigens). In some embodiments, the RBC substrate includes RBCs having a mixture of ABO blood types. In some embodiments, the RBC substrate is homogeneous with respect to Rh factor. In other embodiments, the RBC substrate is heterogeneous with respect to Rh factor. In some embodiments, the RBC substrate is homogeneous with respect to any one or more of the following antigens: $Cs^a$, $Cs^b$, $Er^a$, $Er^b$, Vel. ABTI, Lan, $At^a$, $Jr^a$, AnWj, $Sd^a$, Batty (By), Biles (Bi), Box ($Bx^a$) Christiansen ($Chr^a$), HJK, HOFM, JFV, JONES, Jensen ($Je^a$), Katagiri (Kg), Livesay ($Li^a$), Milne, Oldeide ($Ol^a$), Peters ($Pt^a$), Rasmussen (RASM), Reid ($Re^a$), REIT, SARA, Torkildsen ($To^a$), and Bennett-Goodspeed (Bg). In some embodiments, the RBC substrate is heterogeneous with respect to any one or more of the following antigens: $Cs^a$, $Cs^b$, $Er^a$, $Er^b$, Vel. ABTI, Lan, $At^a$, $Jr^a$, AnWj, $Sd^a$, Batty (By), Biles (Bi), Box ($Bx^a$) Christiansen ($Chr^a$), HJK, HOFM, JFV, JONES, Jensen ($Je^a$), Katagiri (Kg), Livesay ($Li^a$), Milne, Oldeide ($Ol^a$), Peters ($Pt^a$), Rasmussen (RASM), Reid ($Re^a$), REIT, SARA, Torkildsen ($To^a$), and Bennett-Goodspeed (Bg).

RBCs for use as a substrate in the compositions and methods described herein can be obtained by any method known in the art. For instance, RBCs can be obtained by standard RBC donation techniques (e.g., apheresis, double red collection). Alternatively, RBCs can be obtained from whole blood donations via separation of the RBCs from other components of the whole blood, for example, via centrifugation or other standard fractionation technique. In some embodiments, RBCs are sterilized via any method known in the art prior to or after functionalization with the surface-bound moiety.

One skilled in the art would appreciate that a compound can be bound to a substrate in an array in accordance with some embodiments of the present disclosure. As used herein the term "array" refers to a generally ordered arrangement of bound compounds on a substrate such as glass or plastics. Typically the array may be in the form of a series of regularly spaced apart delimited areas to which the compounds are bound. Such arrays may be described as a chip. For example, arrays in multi-well microplates can be scanned by automatic equipment.

Surface-Bound Moiety

In accordance with various embodiments of the present application, a moiety is bound to the surface of a substrate. In some embodiments, the moiety is a pathogen-inactivating compound. In some embodiments, the moiety is a derivative of (e.g., portion of) a pathogen-inactivating compound. In some embodiments, the moiety is a compound with an analogous or common portion to a pathogen-inactivating compound. A substrate can be treated with a pathogen-inactivating compound so that the compound or a derivative thereof is bound to the surface of the substrate. Alternatively, a substrate can be treated with a moiety that itself is a derivative of a pathogen-inactivating compound, such that the reactive moiety itself becomes bound to the substrate, or a further derivative thereof becomes bound to the substrate. Alternatively, a substrate can be treated with a compound with an analogous or common portion to a pathogen-inactivating compound, such that the analogous or common portion becomes bound to the substrate. In some embodiments, the moiety is a derivative of a compound comprising an acridine, such as for example, an acridine mutagen, a monoalkylator, a bis alkylator, an acridine mustard (e.g., 6-Chloro-9-(3-[(2-chloroethyl)ethylamino]propylamino)-2-methoxyacridine, Sigma #12888), or an acridine half mustard (e.g., 6-Chloro-9-[3-(2-chloroethylamino)propylamino]-2-methoxyacridine dihydrochloride, Sigma #I3636), and the substrate can be treated with the compound or derivative of a compound comprising an acridine.

Pathogen-inactivating compounds are compounds that inactivate one or more nucleic acid-containing agents in a red blood cell or other blood-based compositions, which nucleic acid-containing agents are capable of causing disease in a human, other mammals, or vertebrates. The pathogenic agent may be unicellular or multicellular. Examples of pathogens are bacteria, viruses, protozoa, fungi, yeasts, molds, and mycoplasmas which cause disease in humans, other mammals, or vertebrates. The genetic material of the pathogen may be DNA or RNA, and the genetic material may be present as single-stranded or double-stranded nucleic acid.

Pathogen-inactivating compounds have been developed, which typically have electrophilic groups that react with pathogens, more specifically with pathogen nucleic acids. For example, U.S. Pat. Nos. 5,691,132; 6,177,441; 6,410,219; 6,143,490; and 6,093,725, the disclosures of which are hereby incorporated by reference, describe the use of compounds that have a nucleic acid-targeting component as well as an electrophilic component that reacts with the nucleic acid in order to inactivate the pathogen. U.S. Pat. Nos. 6,093,725 and 6,514,987, the disclosures of which are hereby incorporated by reference, describe compounds wherein the nucleic acid-targeting component of the compound is linked to the reactive electrophilic component via a hydrolysable linker. Compounds containing such hydrolysable linkers may be referred to as frangible compounds. Under certain conditions, the linker of a frangible compound will undergo a hydrolysis reaction, thereby de-coupling the nucleic acid-targeting component and the electrophilic component of the compound. Compounds containing a nucleic acid-targeting component bound to an electrophilic component via a non-hydrolysable linker may be referred to as non-frangible compounds.

In some embodiments, pathogen-inactivating compounds include compounds that comprise a functional group which is, or which is capable of forming and has formed, e.g. in situ, a reactive group, such as an electrophilic group. In some cases, the pathogen-inactivating compound requires photoactivation to be reactive. In some cases, the pathogen-inactivating compound does not require photoactivation to be reactive. For example, the functional group may be a mustard group, a mustard group intermediate, a mustard group equivalent, an epoxide, a formaldehyde or a formaldehyde synthon. Such functional groups are capable of forming in situ a reactive group, such as an electrophilic aziridine, aziridinium, thiirane or thiiranium ion. A mustard group may be a mono- or bis-(haloethyl)amine group or a mono (haloethyl)sulfide group. A mustard equivalent is a group that reacts by a mechanism similar to the mustards, for example by forming reactive intermediates such as aziridinium and aziridine groups or thiirane and thiiranium groups. Examples include aziridine derivatives, mono or bis-(mesylethyl)amine groups, mono-(mesylethyl)sulfide groups, mono or bis-(tosylethyl)amine groups and mono-(tosylethyl)sulfide groups. A formaldehyde synthon is any compound that breaks down to a formaldehyde, which includes a hydroxylamine such as hydroxymethylglycine. The reactive group of the pathogen-inactivating compound is capable of reacting with the nucleic acids of pathogens, for example with nucleophilic groups on the nucleic acid. The reactive group is also capable of reacting with a nucleophilic group of a quencher.

In some embodiments, pathogen-inactivating compounds include a component that targets the compound to nucleic acids, such as an anchor portion. The anchor portion comprises a moiety that is capable of binding non-covalently to a nucleic acid biopolymer, such as DNA or RNA, and is also referred to as a nucleic acid binding ligand, nucleic acid binding group, or nucleic acid binding moiety. In certain embodiments, an anchor portion is linked to the reactive electrophilic component via a hydrolysable linker.

In some embodiments, the compound with which a substrate provided herein is treated, or a resultant moiety bound to the surface of a substrate provided herein is a non-frangible compound or a derivative thereof. The non-frangible compounds may be a compound of any of Formulae I, II, or III, as follows.

Formula I is:

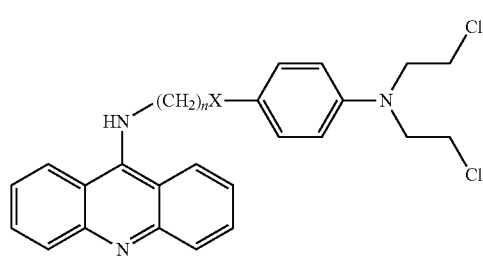

Formula (I)

wherein n is an integer from 1-12, inclusive, and X is CH₂, NH, O, or S, or a salt or stereoisomer (including enantiomers and diastereomers) thereof.

Formula II is:

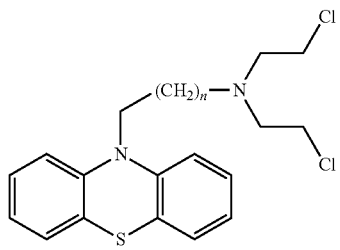

Formula (II)

wherein n is an integer from 1-12, inclusive, or a salt or stereoisomer (including enantiomers and diastereomers) thereof.

Formula III is:

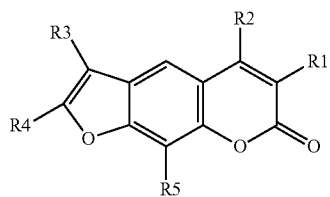

Formula (III)

wherein one or two of R1 R2, R3, R4, and R5 are independently a (2-chloroethyl)amino group or (2-bromoethyl)amino group, optionally with a second 2-ethylhalo group on the amine, attached to the tricyclic ring by a chain of one to nine carbons, wherein the chain optionally contain one or more heteroatoms selected from the group consisting of oxygen, nitrogen, and sulfur, wherein the chain optionally comprises one or more unsaturated bonds or carbonyl groups, and wherein the chain is optionally substituted with one or more lower alkyl groups; and the remaining R1, R2, R3, R4, and R5 are independently hydrogen, lower alkyl, lower alkoxy, halogen, —CH2OR6, or —CH2NR7R8, wherein R6, R7, and R8 are each independently hydrogen or lower alkyl.

Particular non-frangible compounds include the following:

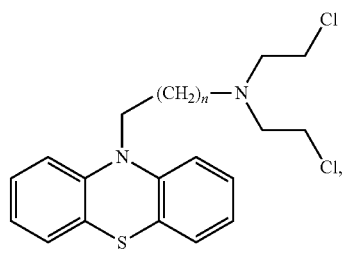

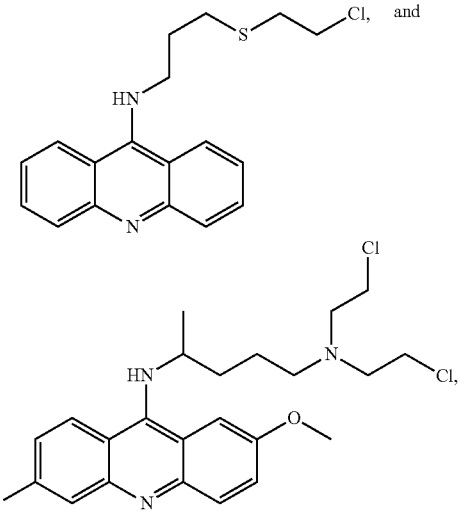

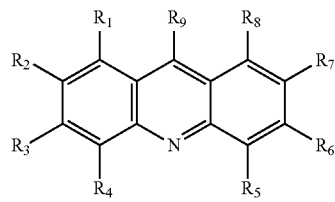

and salts or stereoisomers (including enantiomers and diastereomers) thereof.

In some embodiments, the compound with which a substrate provided herein is treated, or a resultant moiety bound to the surface of a substrate provided herein is a frangible compound or a derivative thereof. The frangible compound may be a compound of any of Formulae IV, V, or VI, or a derivative of a compound of any of Formulae IV, V, or VI, as follows.

Formula IV is:

$$\text{(IV)}$$

wherein at least one of $R_1$, $R_2$, $R_3$, $R_4$, $R_5$, $R_6$, $R_7$, $R_8$ and $R_9$ is —V—W—X-E as defined below, and the remainder of $R_1$, $R_2$, $R_3$, $R_4$, $R_5$, $R_6$, $R_7$, $R_8$ and $R_9$ are independently selected from the group consisting of —H, —$R_{10}$, —O—$R_{10}$, —NO₂, —NH₂, —NH—$R_{10}$, —N($R_{10})_2$, —F, —Cl, —Br, —I, —C(=O)—$R_{10}$, —C(=O)—O—$R_{10}$, and —O—C(=O)—$R_{10}$, where —$R_{10}$ is independently
H, —$C_{1-8}$alkyl, —$C_{1-8}$heteroalkyl, -aryl, -heteroaryl, —$C_{1-3}$alkyl-aryl, —$C_{1-3}$heteroalkyl-aryl, —$C_{1-3}$alkyl-heteroaryl, —$C_{1-3}$heteroalkyl-heteroaryl, -aryl-$C_{1-3}$alkyl, -aryl-$C_{1-3}$heteroalkyl, -heteroaryl-$C_{1-3}$alkyl,-heteroaryl-$C_{1-3}$heteroalkyl, —$C_{1-3}$alkyl-aryl-$C_{1-3}$ alkyl, —$C_{1-3}$heteroalkyl-aryl-$C_{1-3}$ alkyl, —$C_{1-3}$alkyl-heteroaryl-$C_{1-3}$ alkyl, —$C_{1-3}$alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$alkyl-heteroaryl-$C_{1-3}$ heteroalkyl, or —$C_{1-3}$heteroalkyl-heteroaryl-$C_{1-3}$ heteroalkyl;

V is independently —$R_{11}$—, —NH—$R_{11}$— or —N(CH₃)—$R_{11}$—, where —$R_{11}$— is independently —$C_{1-8}$alkyl-, —$C_{1-8}$heteroalkyl-, -aryl-, -heteroaryl-, —$C_{1-3}$alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$heteroalkyl-, -heteroaryl-$C_{1-3}$alkyl-, -heteroaryl-$C_{1-3}$heteroalkyl-, —$C_{1-3}$ alkyl-aryl-$C_{1-3}$ alkyl-, —$C_{1-3}$heteroalkyl-aryl-$C_{1-3}$ alkyl-, —$C_{1-3}$alkyl-heteroaryl-$C_{1-3}$ alkyl-, —$C_{1-3}$alkyl-aryl-$C_{1-3}$ heteroalkyl-, —$C_{1-3}$heteroalkyl-heteroaryl-$C_{1-3}$ alkyl-, —$C_{1-3}$heteroalkyl-aryl-$C_{1-3}$ heteroalkyl-, —$C_{1-3}$alkyl-heteroaryl-$C_{1-3}$ heteroalkyl-, or —$C_{1-3}$heteroalkyl-heteroaryl-$C_{1-3}$ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—NR$_{10}$—, —NR$_{10}$—C(=O)—, —O—P(=O)(—OR$_{10}$)—O—, —P(=O)(—OR$_{10}$)—O—, —O—P(=O)(—OR$_{10}$)—;

X is independently —R$_{11}$—; and

E is independently selected from the group consisting of —N(R$_{12}$)$_2$, —N(R$_{12}$)(R$_{13}$), —S—R$_{12}$, and

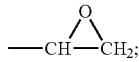

where —R$_{12}$ is —CH$_2$CH$_2$-G, where each G is independently —Cl, —Br, —I, —O—S(=O)$_2$—CH$_3$, —O—S(=O)$_2$—CH$_2$—C$_6$H5, or —O—S(=O)$_2$—C$_6$H$_4$—CH$_3$; and where R$_{13}$ is independently —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$heteroalkyl-heteroaryl, -aryl-$C_{1-3}$alkyl, -aryl-$C_{1-3}$heteroalkyl, -heteroaryl-$C_{1-3}$alkyl, -heteroaryl-$C_{1-3}$heteroalkyl, —$C_{1-3}$alkyl-aryl-$C_{1-3}$ alkyl, —$C_{1-3}$heteroalkyl-aryl-$C_{1-3}$ alkyl, —$C_{1-3}$alkyl-heteroaryl-$C_{1-3}$ alkyl, —$C_{1-3}$alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$alkyl-heteroaryl-$C_{1-3}$ heteroalkyl, or —$C_{1-3}$heteroalkyl-heteroaryl-$C_{1-3}$ heteroalkyl;

or a salt or stereoisomer (including enantiomers and diastereomers) thereof.

In some embodiments of Formula IV, R$_1$, R$_2$, R$_3$, R$_4$, R$_5$, R$_6$, R$_7$, and R$_8$ are each hydrogen. In other embodiments, at least 1, at least 2, at least 3, at least 4, at least 5, at least 6, or at least 7 of R$_1$, R$_2$, R$_3$, R$_4$, R$_5$, R$_6$, R$_7$, R$_8$ are hydrogen.

In some embodiments of Formula IV, R$_9$ is —V—W—X-E. In some embodiments, V is —NH—R$_{11}$—. In some such embodiments, Ru is —$C_{1-8}$alkyl-, e.g., methyl or ethyl. In particular embodiments, V is —NH—R$_{11}$—, wherein R$_{11}$ is a linear —$C_{1-8}$alkyl-. In some embodiments, V is —N(CH$_3$)—R$_{11}$—. In some such embodiments, R$_{11}$ is —$C_{1-8}$ alkyl-, e.g., methyl or ethyl. In particular embodiments, V is —N(CH$_3$)—R$_1$—, wherein R$_{11}$ is a linear —$C_{1-8}$alkyl-.

In some embodiments of Formula IV, W is —C(=O)—O—. In some embodiments, W is —C(=O)—NR$_{10}$—. In some embodiments, W is —C(=O)—NH—.

In some embodiments of Formula IV, X is —R$_{11}$—, wherein —R$_{11}$— is —$C_{1-8}$alkyl-. In some embodiments, X is methyl. In some embodiments, X is ethyl. In some embodiments, X is linear —$C_{1-8}$alkyl-.

In some embodiments of Formula IV, E is —N(R$_{12}$)$_2$, wherein R$_{12}$ is —CH$_2$CH$_2$-G. In some such embodiments, each G is independently —Cl, —Br, or —I. In some such embodiments, both G moieties are —Cl.

In some embodiments of Formula IV, R$_9$ is —NH—$C_{1-8}$alkyl-C(=O)—O—$C_{1-8}$alkyl-N(CH$_2$CH$_2$Cl)$_2$. In some embodiments R$_9$ is —NH—(CH$_2$)—C(=O)—O—(CH$_2$)—N(CH$_2$CH$_2$Cl)$_2$, —NH—(CH$_2$)$_2$—C(=O)—O—(CH$_2$)—N(CH$_2$CH$_2$Cl)$_2$, —NH—(CH$_2$)—C(=O)—O—(CH$_2$)$_2$—N(CH$_2$CH$_2$Cl)$_2$, —NH—(CH$_2$)$_2$—C(=O)—O—(CH$_2$)$_2$—N(CH$_2$CH$_2$Cl)$_2$, —NH—(CH$_2$)$_3$—C(=O)—O—(CH$_2$)—N(CH$_2$CH$_2$Cl)$_2$, or —NH—(CH$_2$)—C(=O)—O—(CH$_2$)$_3$—N(CH$_2$CH$_2$Cl)$_2$. In some such embodiments, each of R$_1$, R$_2$, R$_3$, R$_4$, R$_5$, R$_6$, R$_7$, and R$_8$ is hydrogen.

In some embodiments of Formula IV, R$_9$ is —NH—$C_{1-8}$alkyl-C(=O)—NH—$C_{1-8}$alkyl-N(CH$_2$CH$_2$Cl)$_2$. In some embodiments R$_9$ is —NH—(CH$_2$)—C(=O)—NH—(CH$_2$)—N(CH$_2$CH$_2$Cl)$_2$, —NH—(CH$_2$)$_2$—C(=O)—NH—(CH$_2$)—N(CH$_2$CH$_2$Cl)$_2$, —NH—(CH$_2$)—C(=O)—NH—(CH$_2$)$_2$—N(CH$_2$CH$_2$Cl)$_2$, —NH—(CH$_2$)$_2$—C(=O)—NH—(CH$_2$)$_2$—N(CH$_2$CH$_2$Cl)$_2$, —NH—(CH$_2$)$_3$—C(=O)—NH—(CH$_2$)—N(CH$_2$CH$_2$Cl)$_2$, or —NH—(CH$_2$)—C(=O)—NH—(CH$_2$)$_3$—N(CH$_2$CH$_2$Cl)$_2$. In some such embodiments, each of R$_1$, R$_2$, R$_3$, R$_4$, R$_5$, R$_6$, R$_7$, and R$_8$ is hydrogen.

Formula V is:

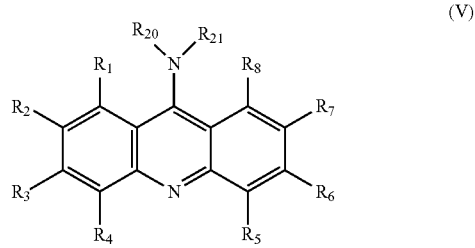

(V)

where R$_1$, R$_2$, R$_3$, R$_4$, R$_5$, R$_6$, R$_7$, and R$_8$ are independently selected from the group consisting of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$, where —R$_{10}$ is independently H, —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$heteroalkyl-heteroaryl, -aryl-$C_{1-3}$alkyl, -aryl-$C_{1-3}$heteroalkyl, -heteroaryl-$C_{1-3}$alkyl, -heteroaryl-$C_{1-3}$heteroalkyl, —$C_{1-3}$alkyl-aryl-$C_{1-3}$ alkyl, —$C_{1-3}$heteroalkyl-aryl-$C_{1-3}$ alkyl, —$C_{1-3}$alkyl-heteroaryl-$C_{1-3}$ alkyl, —$C_{1-3}$alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, or —$C_{1-3}$heteroalkyl-heteroaryl-$C_{1-3}$ heteroalkyl;

R$_{20}$ is —H or —CH$_3$; and

R$_{21}$ is —R$_{11}$—W—X-E, where —R$_{11}$— is independently —$C_{1-8}$alkyl-, —$C_{1-8}$heteroalkyl-, -aryl-, -heteroaryl-, —$C_{1-3}$alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$heteroalkyl-, -heteroaryl-$C_{1-3}$alkyl-, -heteroaryl-$C_{1-3}$heteroalkyl-, —$C_{1-3}$ alkyl-aryl-$C_{1-3}$ alkyl-, —C$_{1-3}$heteroalkyl-aryl-C$_{1-3}$ alkyl-, —C$_{1-3}$alkyl-heteroaryl-C$_{1-3}$ alkyl-, —C$_{1-3}$alkyl-aryl-C$_{1-3}$ heteroalkyl-, —C$_{1-3}$heteroalkyl-heteroaryl-C$_{1-3}$ alkyl-, —C$_{1-3}$heteroalkyl-aryl-C$_{1-3}$
heteroalkyl-, —C$_{1-3}$alkyl-heteroaryl-C$_{1-3}$ heteroalkyl-, or —C$_{1-3}$heteroalkyl-heteroaryl-C$_{1-3}$ heteroalkyl-;
W is
independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—NR$_{10}$—, —NR$_{10}$—C(=O)—, —O—P(=O)(—OR$_{10}$)—O—, —P(=O)(—OR$_{10}$)—O—, —O—P(=O)(—OR$_{10}$)—;
X is independently —R$_{11}$—; and
E is independently selected from the group consisting of —N(R$_{12}$)$_2$, —N(R$_{12}$)(R$_{13}$), —S—R$_{12}$, and

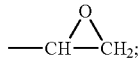

where —R$_{12}$ is —CH$_2$CH$_2$-G, where each G is
independently —Cl, —Br, —I, —O—S(=O)$_2$—CH$_3$, —O—S(=O)$_2$—CH$_2$—C$_6$H$_5$, or —O—S(=O)$_2$—C$_6$H$_4$—CH$_3$;
and where R$_{13}$ is independently —C$_{1-8}$ alkyl, —C$_{1-8}$
heteroalkyl, -aryl, -heteroaryl, —C$_{1-3}$alkyl-aryl, —C$_{1-3}$heteroalkyl-aryl, —C$_{1-3}$alkyl-heteroaryl, —C$_{1-3}$heteroalkyl-heteroaryl, -aryl-C$_{1-3}$alkyl, -aryl-C$_{1-3}$heteroalkyl, -heteroaryl-C$_{1-3}$alkyl, -heteroaryl-C$_{1-3}$heteroalkyl, —C$_{1-3}$alkyl-aryl-C$_{1-3}$ alkyl, —C$_{1-3}$heteroalkyl-aryl-C$_{1-3}$
alkyl, —C$_{1-3}$alkyl-heteroaryl-C$_{1-3}$ alkyl, —C$_{1-3}$alkyl-aryl-C$_{1-3}$
heteroalkyl, —C$_{1-3}$heteroalkyl-heteroaryl-C$_{1-3}$ alkyl, —C$_{1-3}$heteroalkyl-aryl-C$_{1-3}$
heteroalkyl, —C$_{1-3}$alkyl-heteroaryl-C$_{1-3}$ heteroalkyl, or —C$_{1-3}$heteroalkyl-heteroaryl-C$_{1-3}$ heteroalkyl;
or a salt or stereoisomer (including enantiomers and diastereomers) thereof.

In some embodiments of Formula V, R$_1$, R$_2$, R$_3$, R$_4$, R$_5$, R$_6$, R$_7$, and R$_8$ are each hydrogen. In other embodiments, at least 1, at least 2, at least 3, at least 4, at least 5, at least 6, or at least 7 of R$_1$, R$_2$, R$_3$, R$_4$, R$_5$, R$_6$, R$_7$, R$_8$ are hydrogen. In some embodiments of Formula V, R$_{20}$ is H. In some embodiments, R$_{20}$ is —CH$_3$.

In some embodiments of Formula V, R$_{21}$ is —R$_{11}$—W—X-E. In some embodiments, R$_{11}$ is —C$_{1-8}$alkyl-, e.g., methyl or ethyl. In some embodiments, R$_{11}$ is a linear —C$_{1-8}$alkyl-. In some embodiments, R$_{11}$ is —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, or —(CH$_2$)$_8$—.

In some embodiments of Formula V, W is —C(=O)—O—. In some embodiments, W is —C(=O)—NR$_{10}$—. In some embodiments, W is —C(=O)—NH—.

In some embodiments of Formula V, X is —R$_{11}$—, wherein —R$_{11}$— is —C$_{1-8}$alkyl-. In some embodiments, X is methyl or ethyl. In some embodiments, X is a linear —C$_{1-8}$alkyl-. In some embodiments, X is —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, or —(CH$_2$)$_8$—. In some such embodiments, R$_{20}$ is H. In some such embodiments, R$_{20}$ is —CH$_3$.

In some embodiments of Formula V, E is —N(R$_{12}$)$_2$, wherein R$_{12}$ is —CH$_2$CH$_2$-G. In some such embodiments, each G is independently —Cl, —Br, or —I. In some such embodiments, both G moieties are —Cl.

In some embodiments of Formula V, R$_{21}$ is —C$_{1-8}$alkyl-C(=O)—O—C$_{1-8}$alkyl-N(CH$_2$CH$_2$Cl)$_2$. In some embodiments R$_{21}$ is —(CH$_2$)—C(=O)—O—(CH$_2$)—N(CH$_2$CH$_2$Cl)$_2$, —(CH$_2$)$_2$—C(=O)—O—(CH$_2$)—N(CH$_2$CH$_2$Cl)$_2$, —(CH$_2$)—C(=O)—O—(CH$_2$)$_2$—N(CH$_2$CH$_2$Cl)$_2$, —(CH$_2$)$_2$—C(=O)—O—(CH$_2$)$_2$—N(CH$_2$CH$_2$Cl)$_2$, —(CH$_2$)$_3$—C(=O)—O—(CH$_2$)—N(CH$_2$CH$_2$Cl)$_2$, or —(CH$_2$)—C(=O)—O—(CH$_2$)$_3$—N(CH$_2$CH$_2$Cl)$_2$. In some such embodiments, R$_{20}$ is H. In some such embodiments, R$_{20}$ is —CH$_3$. In any of the foregoing embodiments, each of R$_1$, R$_2$, R$_3$, R$_4$, R$_5$, R$_6$, R$_7$, and R$_8$ may be hydrogen.

In some embodiments of Formula V, R$_{21}$ is —C$_{1-8}$alkyl-C(=O)—NH—C$_{1-8}$alkyl-N(CH$_2$CH$_2$Cl)$_2$. In some embodiments R$_{21}$ is —(CH$_2$)—C(=O)—NH—(CH$_2$)—N(CH$_2$CH$_2$Cl)$_2$, —(CH$_2$)$_2$—C(=O)—NH—(CH$_2$)—N(CH$_2$CH$_2$Cl)$_2$, —(CH$_2$)—C(=O)—NH—(CH$_2$)$_2$—N(CH$_2$CH$_2$Cl)$_2$, —(CH$_2$)$_2$—C(=O)—NH—(CH$_2$)$_2$—N(CH$_2$CH$_2$Cl)$_2$, —(CH$_2$)$_3$—C(=O)—NH—(CH$_2$)—N(CH$_2$CH$_2$Cl)$_2$, or —(CH$_2$)—C(=O)—NH—(CH$_2$)$_3$—N(CH$_2$CH$_2$Cl)$_2$. In some such embodiments, R$_{20}$ is H. In some such embodiments, R$_{20}$ is —CH$_3$. In any of the foregoing embodiments, each of R$_1$, R$_2$, R$_3$, R$_4$, R$_5$, R$_6$, R$_7$, and R$_8$ may be hydrogen.

Formula VI is:

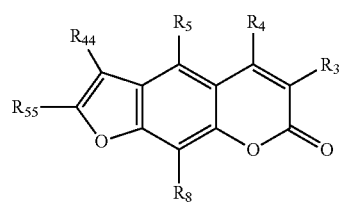

(VI)

wherein at least one of R$_{44}$, R$_{55}$, R$_3$, R$_4$, R$_5$, and R$_8$ is —V—W—X-E, and the remainder of R$_{44}$, R$_{55}$, R$_3$, R$_4$, R$_5$, and R$_8$ are independently selected from the group consisting of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$,
where —R$_{10}$ is independently H, —C$_{1-8}$ alkyl, —C$_{1-8}$
heteroalkyl, -aryl, -heteroaryl, —C$_{1-3}$alkyl-aryl, —C$_{1-3}$heteroalkyl-aryl, —C$_{1-3}$alkyl-heteroaryl, —C$_{1-3}$heteroalkyl-heteroaryl, -aryl-C$_{1-3}$alkyl, -aryl-C$_{1-3}$heteroalkyl, -heteroaryl-C$_{1-3}$alkyl, -heteroaryl-C$_{1-3}$heteroalkyl, —C$_{1-3}$alkyl-aryl-C$_{1-3}$ alkyl, —C$_{1-3}$heteroalkyl-aryl-C$_{1-3}$
alkyl, —C$_{1-3}$alkyl-heteroaryl-C$_{1-3}$ alkyl, —C$_{1-3}$alkyl-aryl-C$_{1-3}$
heteroalkyl, —C$_{1-3}$heteroalkyl-heteroaryl-C$_{1-3}$ alkyl, —C$_{1-3}$heteroalkyl-aryl-C$_{1-3}$ heteroalkyl, —C$_{1-3}$alkyl-heteroaryl-C$_{1-3}$ heteroalkyl, or —C$_{1-3}$heteroalkyl-heteroaryl-C$_{1-3}$ heteroalkyl;
V is independently —R$_{11}$—, —NH—R$_{11}$— or —N(CH$_3$)—R$_{11}$—, where —R$_{11}$— is
independently —C$_{1-8}$alkyl-, —C$_{1-8}$heteroalkyl-, -aryl-, -heteroaryl-, —C$_{1-3}$alkyl-aryl-, —C$_{1-3}$heteroalkyl-aryl-, —C$_{1-3}$alkyl-heteroaryl-, —C$_{1-3}$heteroalkyl-heteroaryl-, -aryl-C$_{1-3}$alkyl-, -aryl-C$_{1-3}$heteroalkyl-, -heteroaryl-C$_{1-3}$alkyl-, -heteroaryl-C$_{1-3}$heteroalkyl-, —C$_{1-3}$ alkyl-aryl-C$_{1-3}$ alkyl-, —C₁₋₃heteroalkyl-aryl-C₁₋₃ alkyl-, —C₁₋₃alkyl-heteroaryl-C₁₋₃ alkyl-, —C₁₋₃alkyl-aryl-C₁₋₃ heteroalkyl-, —C₁₋₃heteroalkyl-heteroaryl-C₁₋₃ alkyl-, —C₁₋₃heteroalkyl-aryl-C₁₋₃ heteroalkyl-, —C₁₋₃alkyl-heteroaryl-C₁₋₃ heteroalkyl-, or —C₁₋₃heteroalkyl-heteroaryl-C₁₋₃ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)₂—O—, —S(=O)₂—O—, —O—S(=O)₂—, —C(=O)—NR₁₀—, —NR₁₀—C(=O)—, —O—P(=O)(—OR₁₀)—O—, —P(=O)(—OR₁₀)—O—, —O—P(=O)(—OR₁₀)—;

X is independently —R₁₁—; and

E is independently selected from the group consisting of —N(R₁₂)₂, —N(R₁₂)(R₁₃), —S—R₁₂, and

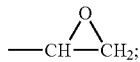

where —R₁₂ is —CH₂CH₂-G, where each G is independently —Cl, —Br, —I, —O—S(=O)₂—CH₃, —O—S(=O)₂—CH₂—C₆H₅, or —O—S(=O)₂—C₆H₄—CH₃;

and where R₁₃ is independently —C₁₋₈ alkyl, —C₁₋₈ heteroalkyl, -aryl, -heteroaryl, —C₁₋₃alkyl-aryl, —C₁₋₃heteroalkyl-aryl, —C₁₋₃alkyl-heteroaryl, —C₁₋₃heteroalkyl-heteroaryl, -aryl-C₁₋₃alkyl, -aryl-C₁₋₃heteroalkyl, -heteroaryl-C₁₋₃alkyl, -heteroaryl-C₁₋₃heteroalkyl, —C₁₋₃alkyl-aryl-C₁₋₃ alkyl, —C₁₋₃heteroalkyl-aryl-C₁₋₃ alkyl, —C₁₋₃alkyl-heteroaryl-C₁₋₃ alkyl, —C₁₋₃alkyl-aryl-C₁₋₃ heteroalkyl, —C₁₋₃heteroalkyl-heteroaryl-C₁₋₃ alkyl, —C₁₋₃heteroalkyl-aryl-C₁₋₃ heteroalkyl, —C₁₋₃alkyl-heteroaryl-C₁₋₃ heteroalkyl, or —C₁₋₃heteroalkyl-heteroaryl-C₁₋₃ heteroalkyl;

or a salt or stereoisomer (including enantiomers and diastereomers) thereof.

It will be appreciated that, in Formula IV above, the acridine nucleus is an anchor moiety, the —V—W—X— group(s) comprises an frangible linker, and the E group(s) is an effector group. Similarly, in Formula VI above, the psoralen nucleus is an anchor moiety, the —V—W—X— group(s) comprises an frangible linker, and the E group(s) is an effector group. Formula V is a subset of Formula IV.

In some embodiments, the frangible compound of Formula IV is a compound of Formula IV(a)-IV(h), or a salt or stereoisomer (including enantiomers and diastereomers) thereof, where all variable groups not specifically indicated are the same as for Formula IV above:

Formula IV(a): W is independently —O—C(=O)—, —C(=S)—O—, —O—C(=S)—, —C(=S)—S—, —S—C(=S)—, —C(=O)—S—, —S—C(=O)—, —O—S(=O)₂—O—, —S(=O)₂—O—, —O—S(=O)₂—, —C(=O)—NR₁₀—, —NR₁₀—C(=O)—, —O—P(=O)(—OR₁₀)—O—, —P(=O)(—OR₁₀)—O—, —O—P(=O)(—OR₁₀)—;

Formula IV(b): V is independently —R₁₁—, or —N(CH₃)—R₁₁—, where —R₁₁— is independently —C₁₋₈alkyl-, -aryl-, -heteroaryl-, —C₁₋₃alkyl-aryl-, —C₁₋₃heteroalkyl-aryl-, —C₁₋₃alkyl-heteroaryl-, —C₁₋₃heteroalkyl-heteroaryl-, -aryl-C₁₋₃alkyl-, -aryl-C₁₋₃heteroalkyl-, -heteroaryl-C₁₋₃alkyl-, -heteroaryl-C₁₋₃heteroalkyl-, —C₁₋₃alkyl-aryl-C₁₋₃ alkyl-, —C₁₋₃heteroalkyl-aryl-C₁₋₃ alkyl-, —C₁₋₃alkyl-heteroaryl-C₁₋₃ alkyl-, —C₁₋₃alkyl-aryl-C₁₋₃ heteroalkyl-, —C₁₋₃heteroalkyl-heteroaryl-C₁₋₃ alkyl-, —C₁₋₃heteroalkyl-aryl-C₁₋₃ heteroalkyl-, —C₁₋₃alkyl-heteroaryl-C₁₋₃ heteroalkyl-, or —C₁₋₃heteroalkyl-heteroaryl-C₁₋₃ heteroalkyl-;

Formula IV(c): —R₁₁— is independently -aryl-, -heteroaryl-, —C₁₋₃alkyl-aryl-, —C₁₋₃heteroalkyl-aryl-, —C₁₋₃alkyl-heteroaryl-, —C₁₋₃heteroalkyl-heteroaryl-, -aryl-C₁₋₃alkyl-, -aryl-C₁₋₃heteroalkyl-, -heteroaryl-C₁₋₃alkyl-, -heteroaryl-C₁₋₃heteroalkyl-, —C₁₋₃alkyl-aryl-C₁₋₃ alkyl-, —C₁₋₃heteroalkyl-aryl-C₁₋₃ alkyl-, —C₁₋₃alkyl-heteroaryl-C₁₋₃ alkyl-, —C₁₋₃alkyl-aryl-C₁₋₃ heteroalkyl-, —C₁₋₃heteroalkyl-heteroaryl-C₁₋₃ alkyl-, —C₁₋₃heteroalkyl-aryl-C₁₋₃ heteroalkyl-, —C₁₋₃alkyl-heteroaryl-C₁₋₃ heteroalkyl-, or —C₁₋₃heteroalkyl-heteroaryl-C₁₋₃ heteroalkyl-;

Formula IV(d): —R₁₂ is —CH₂CH₂-G, where each G is independently —Br, —I, —O—S(=O)₂—CH₃, —O—S(=O)₂—CH₂—C₆H₅, or —O—S(=O)₂—C₆H₄—CH₃;

Formula IV(e): E is independently selected from the group consisting of —N(R₁₂)(R₁₃), —S—R₁₂, and

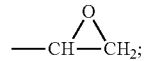

where —R₁₂ is —CH₂CH₂-G, where each G is independently —Cl, —Br, —I, —O—S(=O)₂—CH₃, —O—S(=O)₂—CH₂—C₆H₅, or —O—S(=O)₂—C₆H₄—CH₃; and where R₁₃ is independently —C₁₋₈ heteroalkyl, -aryl, -heteroaryl, —C₁₋₃alkyl-aryl, —C₁₋₃heteroalkyl-aryl, —C₁₋₃alkyl-heteroaryl, —C₁₋₃heteroalkyl-heteroaryl, -aryl-C₁₋₃alkyl, -aryl-C₁₋₃heteroalkyl, -heteroaryl-C₁₋₃alkyl, -heteroaryl-C₁₋₃heteroalkyl, —C₁₋₃alkyl-aryl-C₁₋₃ alkyl, —C₁₋₃heteroalkyl-aryl-C₁₋₃ alkyl, —C₁₋₃alkyl-heteroaryl-C₁₋₃ alkyl, —C₁₋₃alkyl-aryl-C₁₋₃ heteroalkyl, —C₁₋₃heteroalkyl-aryl-C₁₋₃ heteroalkyl, —C₁₋₃alkyl-heteroaryl-C₁₋₃ heteroalkyl, or —C₁₋₃heteroalkyl-heteroaryl-C₁₋₃ heteroalkyl;

Formula IV(f): W is independently —C(=S)—O—, —O—C(=S)—, —C(=S)—S—, —S—C(=S)—, —C(=O)—S—, —S—C(=O)—, —O—S(=O)₂—O—, —S(=O)₂—O—, —O—S(=O)₂—, —C(=O)—NR₁₀—, —NR₁₀—C(=O)—, —O—P(=O)(—OR₁₀)—O—, —P(=O)(—OR₁₀)—O—, —O—P(=O)(—OR₁₀)—;

Formula IV(g): —R₁₂ is —CH₂CH₂-G, where each G is independently —O—S(=O)₂—CH₃, —O—S(=O)₂—CH₂—C₆H₅, or —O—S(=O)₂—C₆H₄—CH₃;

Formula IV(h): at least one of R₁, R₂, R₃, R₄, R₅, R₆, R₇, R₈ and R₉ is —V—W—X-E, as defined for Formula IV, at least one of R₁, R₂, R₃, R₄, R₅, R₆, R₇, R₈ and R₉ is selected from the group consisting of —R₁₀, —O—R₁₀, —NO₂, —NH₂, —NH—R₁₀, —N(R₁₀)₂, —F, —Cl, —Br, —I, —C(=O)—R₁₀, —C(=O)—O—R₁₀, and —O—C(=O)—R₁₀, and at the remainder of R₁, R₂, R₃, R₄, R₅, R₆, R₇, R₈ and R₉ are independently selected from the group consisting of —H, —R₁₀, —O—R₁₀, —NO₂, —NH₂, —NH—R₁₀, —N(R₁₀)₂, —F, —Cl, —Br, —I, —C(=O)—R₁₀, —C(=O)—O—R$_{10}$, and —O—C(=O)—R$_{10}$, wherein R10 is as defined for Formula IV.

In some embodiments, the compound with which a substrate provided herein is treated, or a resultant moiety bound to the surface of a substrate provided herein is a non-frangible compound, such as a non-frangible analog of a compound of any of Formula IV, V, or VI. Such non-frangible compound may be a compound of any of Formula VII, VIII or IX, as follows.

Formula VII is:

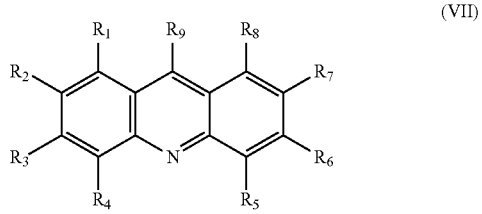

(VII)

wherein at least one of R$_1$, R$_2$, R$_3$, R$_4$, R$_5$, R$_6$, R$_7$, R$_8$ and R$_9$ is —V—X-E where V, X, and E are as defined for Formula IV, and the remainder of R$_1$, R$_2$, R$_3$, R$_4$, R$_5$, R$_6$, R$_7$, R$_8$ and R$_9$ are independently selected from the group consisting
of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$,
where —R$_{10}$ is independently
H, —C$_{1-8}$alkyl, —C$_{1-8}$heteroalkyl, -aryl, -heteroaryl, —C$_{1-3}$alkyl-aryl, —C$_{1-3}$heteroalkyl-aryl, —C$_{1-3}$alkyl-heteroaryl, —C$_{1-3}$heteroalkyl-heteroaryl, -aryl-C$_{1-3}$alkyl, -aryl-C$_{1-3}$heteroalkyl, -heteroaryl-C$_{1-3}$alkyl, -heteroaryl-C$_{1-3}$heteroalkyl, —C$_{1-3}$alkyl-aryl-C$_{1-3}$ alkyl, —C$_{1-3}$heteroalkyl-aryl-C$_{1-3}$
alkyl, —C$_{1-3}$alkyl-heteroaryl-C$_{1-3}$ alkyl, —C$_{1-3}$alkyl-aryl-C$_{1-3}$
heteroalkyl, —C$_{1-3}$heteroalkyl-heteroaryl-C$_{1-3}$ alkyl, —C$_{1-3}$heteroalkyl-aryl-C$_{1-3}$
heteroalkyl, —C$_{1-3}$alkyl-heteroaryl-C$_{1-3}$ heteroalkyl, or —C$_{1-3}$heteroalkyl-heteroaryl-C$_{1-3}$ heteroalkyl.
or a salt or stereoisomer (including enantiomers and diastereomers) thereof.

In some embodiments of Formula VII, R$_1$, R$_2$, R$_3$, R$_4$, R$_5$, R$_6$, R$_7$, and R$_8$ are each hydrogen. In other embodiments, at least 1, at least 2, at least 3, at least 4, at least 5, at least 6, or at least 7 of R$_1$, R$_2$, R$_3$, R$_4$, R$_5$, R$_6$, R$_7$, R$_8$ are hydrogen.

In some embodiments of Formula VII, R$_9$ is —V—X-E, where V, X, and E are as defined for Formula IV. In some embodiments, V is —NH—R$_{11}$—. In some such embodiments, R$_1$ is —C$_{1-8}$alkyl-, e.g., methyl or ethyl. In particular embodiments, V is —NH—R$_{11}$—, wherein R$_{11}$ is a linear —C$_{1-8}$alkyl-. In some embodiments, V is —N(CH$_3$)—R$_{11}$—. In some such embodiments, R$_1$ is —C$_{1-8}$alkyl-, e.g., methyl or ethyl. In particular embodiments, V is —N(CH$_3$)—R$_{11}$—, wherein R$_{11}$ is a linear —C$_{1-8}$alkyl-.

In some embodiments of Formula VII, X is —R$_{11}$—, wherein —R$_{11}$— is —C$_{1-8}$alkyl-. In some embodiments, the moiety —V—X— is —NH—C$_{1-8}$alkyl-. In some embodiments, the moiety —V—X— is —NH—(CH$_2$)—, —NH—(CH$_2$)$_2$—, —NH—(CH$_2$)$_3$—, —NH—(CH$_2$)$_4$—, —NH—(CH$_2$)$_5$—, —NH—(CH$_2$)$_6$—, —NH—(CH$_2$)$_7$—, or —NH—(CH$_2$)$_8$—. In some embodiments, the moiety —V—X— is —N(CH$_3$)—C$_{1-8}$alkyl-. In some embodiments, the moiety —V—X— is —N(CH$_3$)—(CH$_2$)—, —N(CH$_3$)—(CH$_2$)$_2$—, —N(CH$_3$)—(CH$_2$)$_3$—, —N(CH$_3$)—(CH$_2$)$_4$—, —N(CH$_3$)—(CH$_2$)$_5$—, —N(CH$_3$)—(CH$_2$)$_6$—, —N(CH$_3$)—(CH$_2$)$_7$—, or —N(CH$_3$)—(CH$_2$)$_8$—.

In some embodiments of Formula VII, E is —N(R$_{12}$)$_2$, wherein R$_{12}$ is —CH$_2$CH$_2$-G. In some such embodiments, each G is independently —Cl, —Br, or —I. In some such embodiments, both G moieties are —Cl.

In some embodiments of Formula VII, R$_9$ is —NH—C$_{1-8}$alkyl-N(CH$_2$CH$_2$Cl)$_2$. In some embodiments R$_9$ is —NH—(CH$_2$)—N(CH$_2$CH$_2$Cl)$_2$, —NH—(CH$_2$)$_2$—N(CH$_2$CH$_2$Cl)$_2$, —NH—(CH$_2$)$_3$—N(CH$_2$CH$_2$Cl)$_2$, —NH—(CH$_2$)$_4$—N(CH$_2$CH$_2$Cl)$_2$, —NH—(CH$_2$)$_5$—N(CH$_2$CH$_2$Cl)$_2$, —NH—(CH$_2$)$_6$—N(CH$_2$CH$_2$Cl)$_2$, —NH—(CH$_2$)$_7$—N(CH$_2$CH$_2$Cl)$_2$, or —NH—(CH$_2$)$_8$—N(CH$_2$CH$_2$Cl)$_2$. In some such embodiments, each of R$_1$, R$_2$, R$_3$, R$_4$, R$_5$, R$_6$, R$_7$, and R$_8$ is hydrogen.

Formula VIII is:

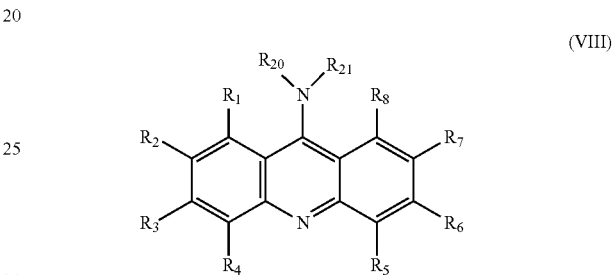

(VIII)

where R$_1$, R$_2$, R$_3$, R$_4$, R$_5$, R$_6$, R$_7$, and R$_8$ are independently selected from the group consisting of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$,
where —R$_{10}$ is independently H, —C$_{1-8}$ alkyl, —C$_{1-8}$ heteroalkyl, -aryl, -heteroaryl, —C$_{1-3}$alkyl-aryl, —C$_{1-3}$heteroalkyl-aryl, —C$_{1-3}$alkyl-heteroaryl, —C$_{1-3}$heteroalkyl-heteroaryl, -aryl-C$_{1-3}$alkyl, -aryl-C$_{1-3}$heteroalkyl, -heteroaryl-C$_{1-3}$alkyl, -heteroaryl-C$_{1-3}$heteroalkyl, —C$_{1-3}$alkyl-aryl-C$_{1-3}$ alkyl, —C$_{1-3}$heteroalkyl-aryl-C$_{1-3}$
alkyl, —C$_{1-3}$alkyl-heteroaryl-C$_{1-3}$ alkyl, —C$_{1-3}$alkyl-aryl-C$_{1-3}$
heteroalkyl, —C$_{1-3}$heteroalkyl-heteroaryl-C$_{1-3}$ alkyl, —C$_{1-3}$heteroalkyl-aryl-C$_{1-3}$
heteroalkyl, —C$_{1-3}$alkyl-heteroaryl-C$_{1-3}$ heteroalkyl, or —C$_{1-3}$heteroalkyl-heteroaryl-C$_{1-3}$ heteroalkyl;
R$_{20}$ is —H or —CH$_3$; and
R$_{21}$ is —R$_{11}$—X-E, where R$_{11}$, X, and E are as defined for Formula V;
or a salt or stereoisomer (including enantiomers and diastereomers) thereof.

In some embodiments of Formula VIII, R$_1$, R$_2$, R$_3$, R$_4$, R$_5$, R$_6$, R$_7$, and R$_8$ are each hydrogen. In other embodiments, at least 1, at least 2, at least 3, at least 4, at least 5, at least 6, or at least 7 of R$_1$, R$_2$, R$_3$, R$_4$, R$_5$, R$_6$, R$_7$, R$_8$ are hydrogen.

In some embodiments of Formula VIII, R$_{20}$ is H. In some embodiments, R$_{20}$ is —CH$_3$.

In some embodiments of Formula VIII, R$_{21}$ is —R$_{11}$—X-E, where R$_{11}$, X, and E are as defined for Formula V. In some embodiments, R$_{11}$ is —C$_{1-8}$alkyl-, e.g., methyl or ethyl. In some embodiments, R$_{11}$ is a linear —C$_{1-8}$alkyl-. In some embodiments, R$_{11}$ is —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, or —(CH$_2$)$_8$—

In some embodiments of Formula VIII, X is —R$_{11}$—, wherein —R$_{11}$— is —C$_{1-8}$alkyl-. In some embodiments, the moiety —R$_{11}$—X— is —C$_{1-8}$alkyl-. In some such embodiments, R$_{20}$ is H. In some such embodiments, R$_{20}$ is —CH$_3$. In some embodiments, the moiety —R$_{11}$—X— is —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, or —(CH$_2$)$_8$—. In some such embodiments, R$_{20}$ is H. In some such embodiments, R$_{20}$ is —CH$_3$.

In some embodiments of Formula VIII, E is —N(R$_{12}$)$_2$, wherein R$_{12}$ is —CH$_2$CH$_2$-G. In some such embodiments, each G is independently —Cl, —Br, or —I. In some such embodiments, both G moieties are —Cl.

In some embodiments of Formula VIII, R$_{21}$ is —C$_{1-8}$ alkyl-N(CH$_2$CH$_2$Cl)$_2$. In some embodiments R$_{21}$ is —(CH$_2$)—N(CH$_2$CH$_2$Cl)$_2$, —(CH$_2$)$_2$—N(CH$_2$CH$_2$Cl)$_2$, —(CH$_2$)$_3$—N(CH$_2$CH$_2$Cl)$_2$, —(CH$_2$)$_4$—N(CH$_2$CH$_2$Cl)$_2$, —(CH$_2$)$_5$—N(CH$_2$CH$_2$Cl)$_2$, —(CH$_2$)$_6$—N(CH$_2$CH$_2$Cl)$_2$, —(CH$_2$)$_7$—N(CH$_2$CH$_2$Cl)$_2$, or —(CH$_2$)$_8$—N(CH$_2$CH$_2$Cl)$_2$. In some such embodiments, R$_{20}$ is H. In some such embodiments, R$_{20}$ is —CH$_3$. In any of the foregoing embodiments, each of R$_1$, R$_2$, R$_3$, R$_4$, R$_5$, R$_6$, R$_7$, and R$_8$ may be hydrogen.

Formula IX is:

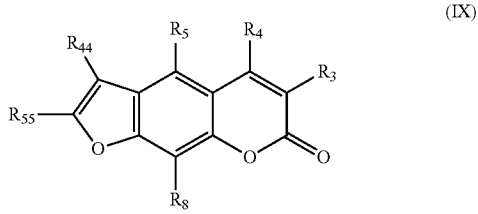

(IX)

wherein at least one of R$_{44}$, R$_{55}$, R$_3$, R$_4$, R$_5$, and R$_8$ is —V—X-E, where V, X, and E are as defined for Formula VI;

and the remainder of R$_{44}$, R$_{55}$, R$_3$, R$_4$, R$_5$, and R$_8$ are independently selected from the group consisting of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$, where —R$_{10}$ is independently H, —C$_{1-8}$ alkyl, —C$_{1-8}$ heteroalkyl, -aryl, -heteroaryl, —C$_{1-3}$alkyl-aryl, —C$_{1-3}$ heteroalkyl-aryl, —C$_{1-3}$alkyl-heteroaryl, —C$_{1-3}$heteroalkyl-heteroaryl, -aryl-C$_{1-3}$alkyl, -aryl-C$_{1-3}$heteroalkyl, -heteroaryl-C$_{1-3}$alkyl, -heteroaryl-C$_{1-3}$heteroalkyl, —C$_{1-3}$alkyl-aryl-C$_{1-3}$ alkyl, —C$_{1-3}$heteroalkyl-aryl-C$_{1-3}$ alkyl, —C$_{1-3}$alkyl-heteroaryl-C$_{1-3}$ alkyl, —C$_{1-3}$alkyl-aryl-C$_{1-3}$ heteroalkyl, —C$_{1-3}$heteroalkyl-heteroaryl-C$_{1-3}$ alkyl, —C$_{1-3}$heteroalkyl-aryl-C$_{1-3}$ heteroalkyl, —C$_{1-3}$alkyl-heteroaryl-C$_{1-3}$ heteroalkyl, or —C$_{1-3}$heteroalkyl-heteroaryl-C$_{1-3}$ heteroalkyl;

or a salt or stereoisomer (including enantiomers and diastereomers) thereof.

A specific example of a suitable pathogen-inactivating compound for use in the present compositions and methods is β-alanine, N-(acridin-9-yl), 2-[bis(2-chloroethyl)amino] ethyl ester (also alternatively referred to herein as "S-303"), the structure of which is as follows, including salts thereof.

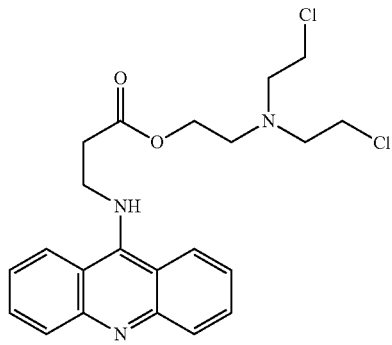

S-303

In some embodiments, the compound with which a substrate provided herein is treated, or a resultant moiety bound to the surface of a substrate provided herein is S-303. In some embodiments, the compound with which a substrate provided herein is treated, or a resultant moiety bound to the surface of a substrate provided herein is a derivative of S-303. In some embodiments, the compound with which a substrate provided herein is treated, or a resultant moiety bound to the surface of a substrate provided herein is a non-frangible analog of S-303 or a derivative thereof.

In some embodiments, the compound with which a substrate provided herein is treated, or a resultant moiety bound to the surface of a substrate provided herein is a compound selected from the following compounds, or a salt or stereoisomer (including enantiomers and diastereomers) thereof:

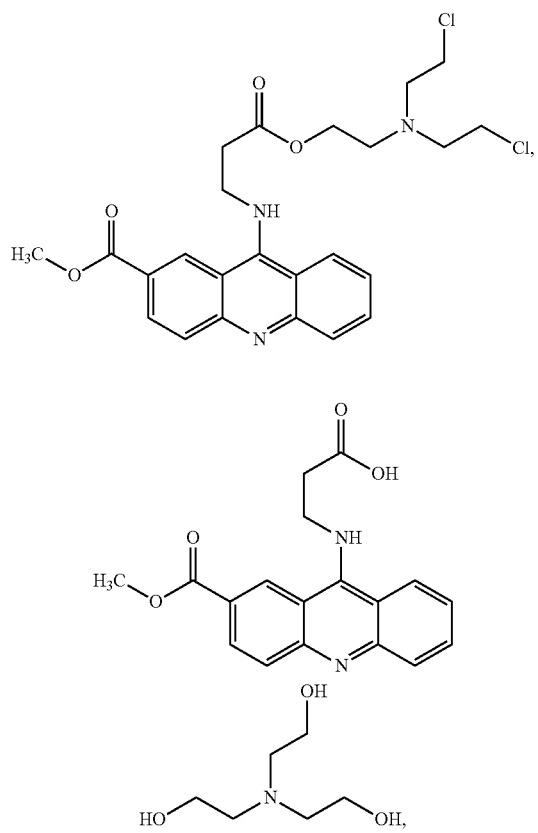

25
-continued
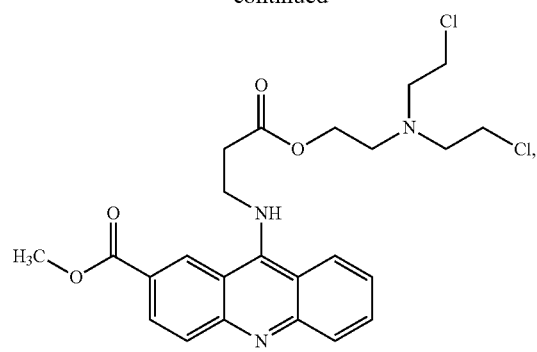
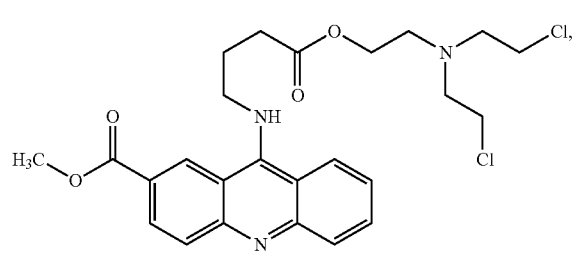
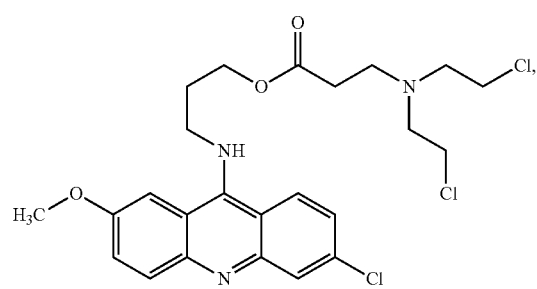
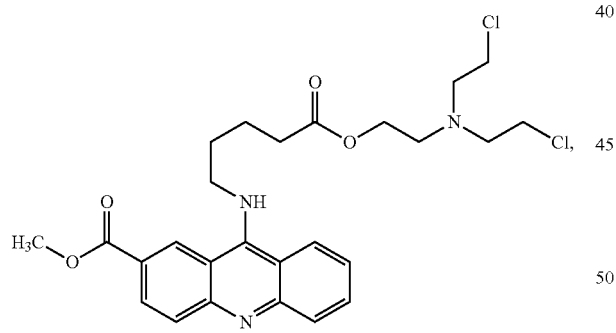
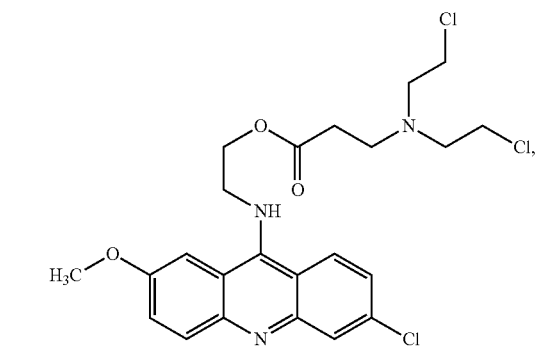
26
-continued
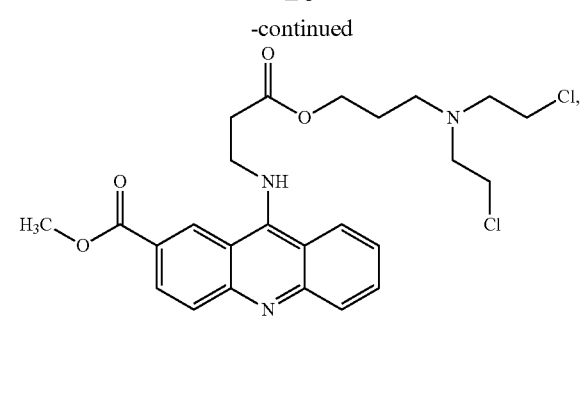
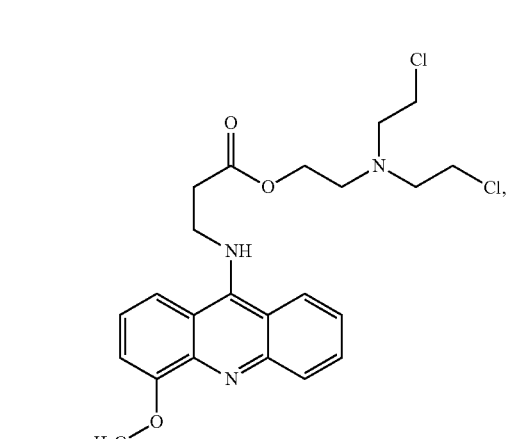
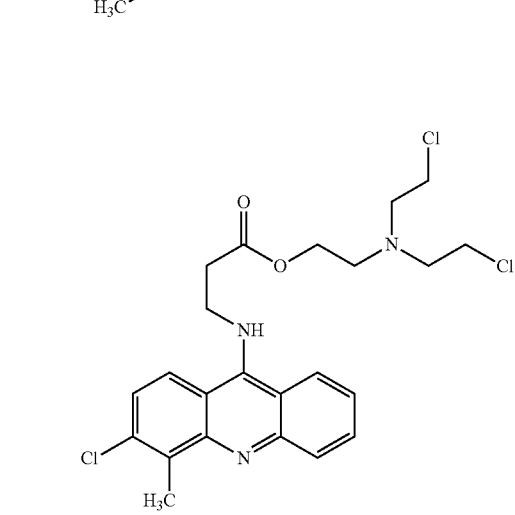
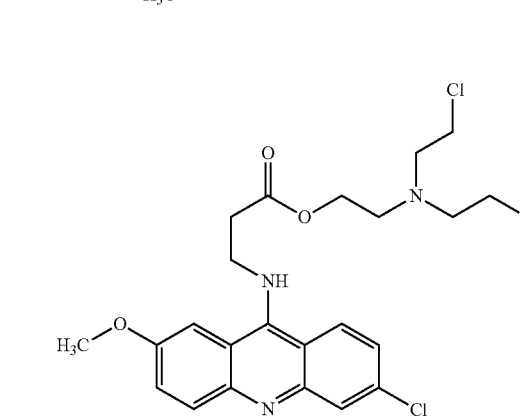

-continued

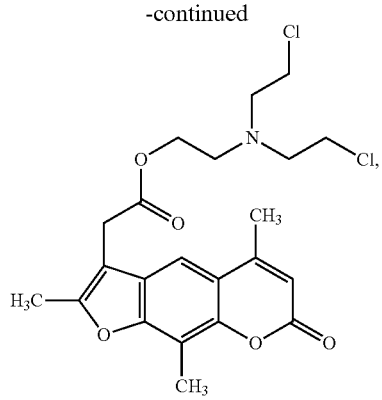

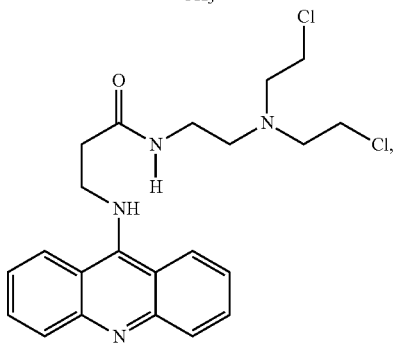

(S-197)

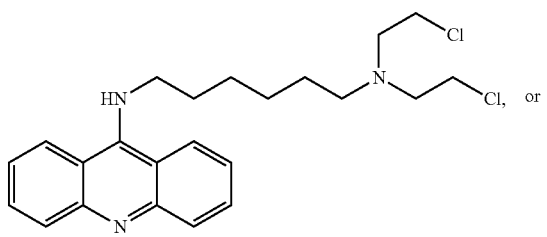

(S-220)

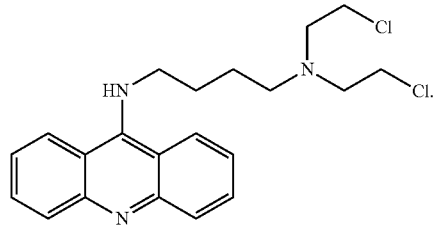

In some embodiments of any of the aforementioned compounds, the compound is a chloride salt. In some embodiments of any of the aforementioned compounds, the compound is a dihydrochloride salt. In some embodiments, the compound a dihydrochloride salt of S-197. In some embodiments, the compound is a dihydrochloride salt of S-220.

In some embodiments, the compound with which a substrate provided herein is treated, or a resultant moiety bound to the surface of a substrate provided herein is a derivative (e.g., a hydrolyzed derivative) of any of the foregoing compounds. In some embodiments, the compound with which a substrate provided herein is treated, or a resultant moiety bound to the surface of a substrate provided herein is a non-frangible analog of any of the foregoing compounds.

A derivative of a compound provided herein may include a nucleic acid-targeting moiety, a portion of a nucleic acid-targeting moiety, an electrophilic moiety, or a portion of an electrophilic moiety. A derivative of a compound provided herein may include a) a nucleic acid-targeting moiety or a portion of a nucleic acid-targeting moiety, and b) an electrophilic moiety or a portion of an electrophilic moiety. A derivative of a compound provided herein may include only a nucleic acid-targeting moiety or a portion of a nucleic acid-targeting moiety. A derivative of a compound provided herein may include only an electrophilic moiety or a portion of an electrophilic moiety. Where the compound is non-frangible, a derivative thereof may include a) a nucleic acid-targeting moiety or a portion of a nucleic acid-targeting moiety, and b) an electrophilic moiety or a portion of an electrophilic moiety, wherein a) and b) are bound to one another via a non-hydrolysable linker. Where the compound is frangible, a derivative thereof may include a) a nucleic acid-targeting moiety or a portion of a nucleic acid-targeting moiety, and b) an electrophilic moiety or a portion of an electrophilic moiety, wherein a) and b) are bound to one another via a hydrolysable linker. Where the compound is frangible, a derivative thereof may include a) a nucleic acid-targeting moiety or a portion of a nucleic acid-targeting moiety bound to a moiety representing the hydrolysis product of a hydrolysable linker. Where the compound is frangible, a derivative thereof may include an electrophilic moiety or a portion of an electrophilic moiety bound to a moiety representing the hydrolysis product of a hydrolysable linker. Moieties representing hydrolysis products include, without limitation, alcohols, amines carboxylic acids, esters, and salts or stereoisomers of any of the foregoing.

Any of the compounds or derivatives described herein may be the starting material for reaction with a substrate in order to form any of the compositions provided herein. Alternatively, any of the compounds or derivatives described herein may be bound to the substrate in any of the compositions provided herein. Any derivative provided herein may be formed from the compound of which it is a derivative, or an equivalent molecular structure may be prepared (e.g., synthesized) independently of the compound of which it is a derivative.

It is understood that a given substrate unit, (e.g., a single red blood cell, a single polystyrene bead), will contain one or more surface-bound moieties. The surface-bound moieties may be homogeneous over a given substrate unit. Alternatively, the surface-bound moieties may be heterogeneous over a given substrate unit (e.g., red blood cell). Heterogeneity over a given substrate unit may result from reaction of the substrate unit with a heterogeneous set of compounds or derivatives. Heterogeneity over a given substrate unit may also result from reaction of the substrate unit with a homogeneous compound or derivative, wherein the reaction of the compound or derivative with the substrate results in a two or more different reaction products bound to the surface of the substrate. In some instances, the surface-bound moieties may be homogenous over any particular substrate unit but heterogeneous over a collection of substrate units (e.g., red blood cells). This may result from reaction of different substrate units with different compounds or derivatives, followed by mixing of the resultant substrate units to form a heterogeneous collection of surface-bound substrate units (e.g., red blood cells).

In any of the embodiments described herein, the surface-bound moiety may be present in an amount on the surface of a substrate, also referred to as the loading level of the substrate. The loading level may be described on a per substrate unit basis, such as for example, on a per cell (e.g., red blood cell), per bead or per particle basis (e.g., moieties per cell, moieties per bead, moieties per particle). In some embodiments, the loading level of the substrate may be at least about 1,000, at least about 2,000, at least about 3,000, at least about 4,000, at least about 5,000, at least about 6,000, at least about 8,000, at least about 10,000, at least about 12,000, at least about 14,000, at least about 17,000, at least about 20,000, at least about 25,000, at least about 30,000, at least about 35,000, at least about 40,000, or at least about 50,000 moieties per substrate unit (e.g., per red blood cell). In some embodiments, the loading level of the substrate may be no more than about 50,000, about 75,000 or about 100,000 moieties per substrate unit (e.g., per red blood cell). In some embodiments, the loading level of the substrate may be between about 1,000 and about 100,000, about 1,000 and about 75,000, about 1,000 and about 50,000, about 1,000 and about 25,000, about 5,000 and about 50,000, about 5,000 and about 25,000, about 5,000 and about 15,000, about 8,000 and about 15,000, about 25,000 and about 50,000, about 25,000 and about 40,000, about 25,000 and about 35,000, about 25,000 and about 30,000, about 30,000 and about 40,000, or about 30,000 and about 35,000 moieties per substrate unit (e.g., per red blood cell). In some embodiments, the loading level of substrate may be about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 20,000, about 22,000, about 24,000, about 26,000, about 28,000, about 30,000, about, about 32,000, about 35,000, about 40,000, about 45,000, about 50,000, about 60,000, about 70,000, about 80,000, about 90,000, or about 100,000 moieties per substrate unit (e.g., per red blood cell).

The loading level may be described on a per unit area basis, such as for example per unit surface area basis (e.g., moieties per $\mu m^2$ substrate surface area). In some embodiments, the loading level of the substrate may be at least about 5, at least about 7, at least about 10, at least about 15, at least about 20, at least about 25, at least about 30, at least about 35, at least about 40, at least about 50, at least about 60, at least about 70, at least about 80, at least about 90, at least about 100, at least about 120, at least about 140, at least about 160, at least about 180, at least about 200, at least about 225, at least about 250, at least about 275, at least about 300, at least about 350, at least about 400, at least about 450, or at least about 500 moieties/$\mu m^2$. In some embodiments, the loading level of the substrate may be no more than about 500, about 750, or about 1,000 moieties/$\mu m^2$. In some embodiments, the loading level of the substrate may be between about 5 and about 1,000, about 5 and about 750, about 5 and about 500, about 20 and about 500, about 20 and about 400, about 20 and about 200, about 20 and about 100, about 30 and about 200, about 30 and about 100, about 50 and about 100, about 100 and about 500, about 100 and about 400, about 140 and about 400, about 140 and about 300, about 140 and about 250 or about 180 and about 300 moieties/$\mu m^2$. In some embodiments, the loading level of the substrate may be about 5, about 7, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, or about 1,000 moieties/$cm^2$.

The loading level may be substantially homogeneous across a collection of substrate units, or it may be heterogeneous across a collection of substrate units. The loading levels provided herein may represent a weighted average loading level across a collection of substrate units. Loading level may be measured by any method known in the art, for example, by labeling (e.g., radiolabeling, immunolabeling, chemical labeling, chemiluminescence, fluorescence labeling) a compound prior to adding to a substrate and then detecting the label after combining the compound with the substrate. Alternatively or in addition, loading level may be measured by directly or indirectly labeling (e.g., immunolabeling, immunofluorescence, chemiluminescence) a compound after adding to a substrate and then detecting the label. Generally, such labeling is performed separately (e.g., as control, as standard curve) from the compound used in the kits and methods provided herein, as a comparator or point of reference in determining the absolute loading levels or relative loading levels. Such labeling may be directly quantitated using a quantitative or semi-quantitative method, or may be compared to a reference standard, such as for example cells, beads or other materials with a known amount of similarly labeled molecule on the surface (e.g., FACS analysis).

In some embodiments, the composition (e.g., moiety-bound substrate) is stable at room temperature. In some embodiments, the composition is stable at refrigeration temperature (e.g., 2-8° C.). In some embodiments, the composition is stable at 0° C. and/or less than 0° C. (e.g., −20° C.). In some embodiments, the composition is stable at −80° C. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 4 months, about 6 months, about 9 months, or about 12 months or longer at room temperature. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 4 months, about 6 months, about 9 months, or about 12 months or longer at refrigeration temperature. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 3 months, about 6 months, about 9 months, or about 1 year or longer at 0° C. and/or less than 0° C. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 3 months, about 6 months, about 9 months, or about 1 year or longer at −80° C. The composition may be stored in the presence of a liquid, a buffer, or any suitable solution (e.g., a non-reactive solution). For instance, where the substrate is red blood cells, the composition may be stored in red blood cell additive solution, blood bank saline, buffered suspension medium, or other suitable solution. Red blood cell additive solutions and buffered suspension medium are known in the art. Where the substrate is red blood cells, the compositions may be stored as a suspension of about 0.3% to about 10% RBCs, about 0.5% to about 5% RBCs, about 0.5% to about 1% RBCs, about 1% to about 1.5% RBCs, about 1.5% to about 2%

RBCs, about 2% to about 2.5% RBCs, about 2.5% to about 3% RBCs, about 3% to about 3.5% RBCs, about 3.5% to about 4% RBCs, about 4% to about 4.5% RBCs, about 4.5% to about 5% RBCs, or about 0.5%, about 1%, about 1.5%, about 2%, about 2.5%, about 3%, about 3.5%, about 4%, about 4.5%, or about 5% RBCs. If the composition will be frozen for storage, a cryopreservative may also be added, such as for example, any cryopreservative known in the art.

The stability and suitability for storage of the compositions (e.g., moiety-bound substrates) provided herein may depend upon the nature of the surface-bound moiety. For instance, a surface-bound moiety lacking a hydrolysable linker (e.g., a non-frangible compound or derivative thereof, or a hydrolysis product of a frangible compound) may be more stable than a surface-bound moiety containing a hydrolysable linker (e.g., a frangible compound or derivative thereof). In some embodiments, a composition provided herein containing a surface-bound moiety lacking a hydrolysable linker is stable at room temperature. In some embodiments, the composition is stable at refrigeration temperature. In some embodiments, the composition is stable at 0° C. and/or less than 0° C. In some embodiments, the composition is stable at −80° C. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 4 months, about 6 months, about 9 months, or about 12 months or more at room temperature. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 4 months, about 6 months, about 9 months, or about 12 months or more at refrigeration temperature. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 3 months, about 6 months, about 9 months, or about 1 year or more at 0° C. and/or less than 0° C. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 3 months, about 6 months, about 9 months, or about 1 year or more at −80° C. In some embodiments, a composition provided herein containing a surface-bound moiety containing a hydrolysable linker is stable at room temperature. In some embodiments, the composition is stable at refrigeration temperature. In some embodiments, the composition is stable at 0° C. and/or less than 0° C. In some embodiments, the composition is stable at −80° C. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 4 months, about 6 months, about 9 months, or about 12 months or more at room temperature. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 4 months, about 6 months, about 9 months, or about 12 months or more at refrigeration temperature. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, about 5 weeks, about 2 months, about 3 months, about 6 months, about 9 months, or about 1 year or more at 0° C. and/or less than 0° C. The composition may be suitable for suitable for storage for at least about 1 hour, about 2 hours, about 4, hours, about 12, hours, about 24 hours, about 48 hours, about 72 hours, about 1 week, about 2 weeks, about 3 weeks, about 4 weeks, 2 months, about 3 months, about 6 months, 9 months, or about 1 year or more at −80° C.

Kits

Provided herein are various kits which comprise any of the compositions (e.g., substrates having surface-bound moieties) described herein. In some embodiments, the kit comprises instruction materials that describe use of the substrates and/or substrates having surface-bound moieties to perform the any of the methods described herein. Kits may also contain any combination of additional components that may be necessary or useful for carrying out any of the methods described herein. Although exemplary kits are described here, the contents of other useful kits will be apparent to the skilled artisan in light of the present disclosure.

Provided herein is a kit for detecting the presence of an antibody in a biological sample in accordance with the methods described herein. In some embodiments, the kit includes a first container that contains a first substrate, wherein a moiety is bound to the surface of the first substrate, and wherein the moiety is selected from the compounds and derivatives thereof described herein; and a second container that contains a second substrate, wherein the surface of the second substrate lacks the bound moiety. The moiety bound to the surface of the first substrate may be any compound or derivative described herein, such as a pathogen-inactivating compound or derivative thereof. In some embodiments, the moiety bound to the surface of the first substrate is S-303 or a derivative thereof. In some embodiments, the moiety bound to the surface of the first substrate is a non-frangible analog of S-303 or a derivative thereof. In some embodiments, the moiety bound to the surface of the first substrate is selected from the group consisting of compounds of Formulae I, II, III, IV, IV(a)-IV(h), V, VI, VII, VIII, and XI, and derivatives thereof, and salts and solvates of any of the foregoing. In some embodiments, the moiety bound to the surface of the first substrate is selected from the group consisting of compounds of Formulae I, II, III, VII, VIII, and XI, and derivatives thereof, and salts and solvates of any of the foregoing. In some embodiments, the moiety bound to the surface of the first substrate is selected from the group consisting of compounds of Formulae IV, V, and VI, and derivatives thereof, and salts and solvates of any of the foregoing. In some embodiments, the moiety bound to the surface of the first substrate is selected from the group consisting of compounds of Formulae IV(a)-IV(h), and derivatives thereof, and salts and solvates of any of the foregoing.

The first and second substrates can be composed of any suitable substrate material, such as any substrate material described herein. The first and second substrates can be composed of cells (e.g., red blood cells). Alternatively, the first and second substrates can be composed of cell membranes or cell-derived material. For example, the first and second substrates may comprise membrane preparations deriving from red blood cells, for example red cell ghosts (i.e. membranes of lysed red cells). Alternatively, the first and second substrates can be composed of a solid support. As described herein, the solid support can be composed of a material (e.g., biological, synthetic) or matrix including, without limitation, polymers or copolymers (e.g., polyesters, polyethers, polyolefins, polyamides, polysaccharides, polyurethanes, styrenes and styrene derivatives, polystyrenes, celluloses), plastic, glass, gold and other metals, etc. A solid support can present the surface-bound moiety in a two-dimensional format (e.g., a plate, multi-well plate) or a three-dimensional formal (e.g., a cell, a bead or other spherical or quasi-spherical object). A substrate can be a portion of an assay plate. Particular solid supports are composed of one or more materials to which the biological sample will not bind or will not substantially find. For instance, the solid support may be composed of a material to which antibodies (e.g., antibodies specific for the compound or portions thereof) do not bind or do not substantially bind. In particular, the solid support is composed of a material to which antibodies against pathogen-inactivated red blood cells do not bind or do not substantially bind. Typically, the first and second substrates will be composed of the same material. In some embodiments, the first and second substrates may comprise red blood cells or membrane preparations derived therefrom immobilized on the surface of a solid support, such as for example an aforementioned solid support. Red blood cells or membrane preparations may be immobilized on the surface of a solid support in a variety of ways known in the art, such as for example, by means of an antibody to a non-blood group antigen expressed on the cell surface or by adhesion using poly-L-lysine, organic dyes or lectins (e.g., lectins having specificity for galactosyl moieties). Preferably, the reagent used is compatible with the cell surface and able to stably maintain binding of the cells or membranes to the solid support throughout assay methods.

In some embodiments, the first and second substrates are both red blood cells. The RBCs of the first and second substrates can be obtained from one or more common donors or from different blood donors. In some instances, the RBCs of the first substrate and the RBCs of the second substrate have one or more property in common, such as ABO blood group (e.g., blood type O), Rh type, or the presence or absence of other RBC antigens (e.g., common RBC antigens, clinically significant RBC antigens, clinically relevant RBC antigens). In other instances, the RBCs of the first substrate and the RBCs of the second substrate differ with respect to certain properties, such as ABO blood group or the presence or absence of other RBC antigens (e.g., common RBC antigens, clinically relevant RBC antigens). In some embodiments, the first and second substrates exhibit one or more antigens commonly found in a biological sample (e.g., whole blood, red blood cells, serum, or plasma). The presence of such an antigen can serve as a control to indicate that the biological sample is making appropriate contact with the first and/or second substrate.

The loading level of the surface-bound moiety on the first substrate (e.g., red blood cells) may be any loading level described herein, such as for example, a loading level sufficient for detection of antibodies to the compound or moieties thereof. In some embodiments, the loading level of the first substrate may be at least about 1,000, at least about 2,000, at least about 3,000, at least about 4,000, at least about 5,000, at least about 6,000, at least about 8,000, at least about 10,000, at least about 12,000, at least about 14,000, at least about 17,000, at least about 20,000, at least about 25,000, at least about 30,000, at least about 35,000, at least about 40,000, or at least about 50,000 moieties per substrate unit (e.g., per red blood cell). In some embodiments, the loading level of the first substrate may be no more than about 50,000, about 75,000 or about 100,000 moieties per substrate unit (e.g., per red blood cell). In some embodiments, the loading level of the first substrate may be between about 1,000 and about 100,000, about 1,000 and about 75,000, about 1,000 and about 50,000, about 1,000 and about 25,000, about 5,000 and about 50,000, about 5,000 and about 25,000, about 5,000 and about 15,000, about 8,000 and about 15,000, about 25,000 and about 50,000, about 25,000 and about 40,000, about 25,000 and about 35,000, about 25,000 and about 30,000, about 30,000 and about 40,000, or about 30,000 and about 35,000 moieties per substrate unit (e.g., per red blood cell). In some embodiments, the loading level of the first substrate may be about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 20,000, about 22,000, about 24,000, about 26,000, about 28,000, about 30,000, about, about 32,000, about 35,000, about 40,000, about 45,000, about 50,000, about 60,000, about 70,000, about 80,000, about 90,000, or about 100,000 moieties per substrate unit (e.g., per red blood cell). In some embodiments, the loading level of the first substrate may be at least about 5, at least about 7, at least about 10, at least about 15, at least about 20, at least about 25, at least about 30, at least about 35, at least about 40, at least about 50, at least about 60, at least about 70, at least about 80, at least about 90, at least about 100, at least about 120, at least about 140, at least about 160, at least about 180, at least about 200, at least about 225, at least about 250, at least about 275, at least about 300, at least about 350, at least about 400, at least about 450, or at least about 500 moieties/$\mu m^2$. In some embodiments, the loading level of the first substrate may be no more than about 500, about 750, or about 1,000 moieties/$\mu m^2$. In some embodiments, the loading level of the first substrate may be between about 5 and about 1,000, about 5 and about 750, about 5 and about 500, about 20 and about 500, about 20 and about 400, about 20 and about 200, about 20 and about 100, about 30 and about 200, about 30 and about 100, about 50 and about 100, about 100 and about 500, about 100 and about 400, about 140 and about 400, about 140 and about 300, about 140 and about 250 or about 180 and about 300 moieties/$\mu m^2$. In some embodiments, the loading level of the first substrate may be about 5, about 7, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, or about 1,000 moieties/$cm^2$. Typically, the loading level of the first substrate will be sufficient for detection of antibodies in a biological sample. In particular, the loading level will be sufficient to distinguish a biological sample from a patient who has or is expected to have an immune response (e.g., pre-existing antibodies) to a pathogen-inactivated red blood cell (e.g., RBC administered by infusion) from a biological sample from a patient who does not have or is not expected to have an immune response (e.g., pre-existing antibodies) to the pathogen-inactivated red blood cell (e.g., RBC administered by infusion).

The kit may further include a third container that contains a third substrate, wherein a first level of the moiety is bound to the surface of the first substrate, a second level of the moiety is bound to the third substrate, and the second level is less than the first level. It would be understood by one of ordinary skill in the art, the second level of the moiety can provide an internal reference for detection of the antibody to the surface-bound moiety at the first level of the moiety. Accordingly, in some embodiments, the relative loading levels of the first and third substrates will be sufficient to distinguish a biological sample from a patient who has or is expected to have an immune response (e.g., pre-existing antibodies) to a pathogen-inactivated red blood cell (e.g., RBC administered by infusion) from a biological sample from a patient who does not have or is not expected to have an immune response (e.g., pre-existing antibodies) to the infused pathogen-inactivated red blood cells. The loading level of the first substrate may be at least about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold, about 250-fold, about 500-fold, 1,000-fold, about 5,000-fold, or about 10,000-fold or more higher than the loading level of the third substrate. In some embodiments, the loading level of the first substrate is between about 2-fold and about 500-fold, about 2-fold and about 100-fold, about 2-fold and about 50-fold, about 2-fold and about 20-fold, about 2-fold and about 10-fold, about 2-fold and about 5-fold, about 4-fold and about 100-fold, about 4-fold and about 50-fold, about 4-fold and about 20-fold, or about 4-fold and about 10-fold higher than the loading level of the third substrate. In some embodiments the loading level of the first substrate is at least about 100, about 110, about 120, about 130, about 140, about 150, about 160, about 180, about 200, about 225, about 250, about 275, about 300, about 325, about 350, about 400, about 450, about 500 moieties/$\mu m^2$, and the loading level of the third substrate is no more than about 100, about 90, about 80, about 70, about 60, about 50, about 40, about 30 moieties/$\mu m^2$. In some embodiments, the loading level of the first substrate is between about 110 and about 750, about 110 and about 500, about 110 and about 400, about 110 and about 300, about 140 and about 750, about 140 and about 500, about 140 and about 400, about 140 and about 300, about 200 and about 400, about 200 and about 300 moieties/$\mu m^2$, and the loading level of the third substrate is between about 10 and about 100, about 20 and about 100, about 30 and about 100, about 40 and about 100, about 50 and about 100 moieties/$\mu m^2$. In some embodiments the loading level of the first substrate is about 110, about 120, about 130, about 140, about 150, about 160, about 180, about 200, about 225, about 250, about 275, about 300, about 325, about 350, about 400, about 450, about 500 moieties/$\mu m^2$, and the loading level of the third substrate is about 10, about 20, about 30, about 40, about 50, about 60, about 70, about 80, about 90, about 100 moieties/$\mu m^2$. In some embodiments the loading level of the first substrate is at least about 15,000, about 17,000, about 20,000, about 25,000, about 30,000, about 40,000, or about 50,000 moieties per substrate unit (e.g., red blood cell), and the loading level of the third substrate is no more than about 14,000, about 12,000, about 10,000, about 8,000, about 6,000, or about 5,000 moieties per substrate unit (e.g., red blood cell). In some embodiments, the loading level of the first substrate is between about 15,000 and about 75,000, about 17,000 and about 75,000, about 20,000 and about 75,000, about 25,000 and about 75,000, about 30,000 and about 75,000, about 40,000 and about 75,000, about 15,000 and about 50,000, about 17,000 and about 50,000, about 20,000 and about 50,000, about 25,000 and about 50,000, about 30,000 and about 50,000, about 40,000 and about 50,000 moieties per substrate unit (e.g., red blood cell), and the loading level of the third substrate is between about 1,000 and about 15,000, about 3,000 and about 15,000, about 5,000 and about 15,000, about 10,000 and about 15,000, about 1,000 and about 14,000, about 3,000 and about 14,000, about 5,000 and about 14,000, about 7,000 and about 14,000, about 10,000 and about 14,000, about 5,000 and about 12,000, about 5,000 and about 10,000 moieties per substrate unit (e.g., red blood cell). In some embodiments the loading level of the first substrate is about 15,000, about 17,000 about 20,000, about 25,000, about 30,000, about 35,000, about 40,000, about 45,000, about 50,000, about 60,000, about 75,000 moieties per substrate unit (e.g., red blood cell), and the loading level of the third substrate is about 1,000, about 3,000, about 5,000, about 7,000, about 10,000, about 12,000, about 14,000 moieties per substrate unit (e.g., red blood cell). Loading levels as disclosed herein may include absolute amounts, such as those set forth above, or relative loading levels, such as the loading level of a first substrate relative to a third substrate.

Typically the third substrate will be composed of the same material as the first and/or second substrates. In some embodiments, the first, second, and third substrates are the same. In the case where there is heterogeneity in the chemical structure or binding chemistry of the surface-bound moiety on the first and third substrates, the third substrate may have the same or different distribution of surface-bound moieties as the first substrate. In some embodiments, the first, second, and third substrates are composed of RBCs, and the RBCs of these three substrates are obtained from one or more common donors. In some embodiments, the first, second, and third substrates all exhibit one or more antigens commonly found in a biological sample (e.g., whole blood, red blood cells, serum, or plasma).

In addition to a primary panel as described herein, a secondary panel can be used in accordance with some embodiments of the present invention. The RBCs of the secondary panel may be obtained from one or more common donors. The RBCs of the secondary panel may be obtained from the same or different donors as the RBCs of the primary panel. The surface-bound moieties of the second panel may be the same as or different from the surface-bound moieties of the first panel. The surface-bound moieties of the secondary panel may be the same as the surface-bound moieties of the first panel, and the loading levels for the two panels may be the same or different. The substrates of the first and second panels may exhibit additional antigens, such as one or more antigens commonly found in a biological sample (e.g., whole blood, red blood cells, serum, or plasma). The additional antigens of the first panel may be the same as or different from the additional antigens of the second panel.

The first, second, and optional third containers of the kits provided herein may be made of any material suitable for storage of first, second, and optional third substrates, which may or may not have surface-bound moieties. The containers may be made of glass, plastic, or any suitable polymeric material. The containers may be sterile and may further provide an environment for maintaining sterility of the contents of the containers. It is understood that the containers will be suitable for storing the contents thereof at an appropriate temperature (e.g., room temperature, refrigeration temperature, freezing temperature, 0° C., −20° C., −80° C.).

The kits provided herein may further contain additive solutions, buffers, or other solutions that may be used in carrying out any of the methods provided herein. The additive solutions, buffers, or other solutions may be useful for storage of the substrates (e.g., substrates containing surface-bound moieties or substrates lacking surface-bound moieties) of the kits. The additive solutions, buffers, or other solutions may be useful in the process of contacting the substrates (e.g., substrates containing surface-bound moieties or substrates lacking surface-bound moieties) of the kits with one or more biological samples. Depending upon the intended use of the additive solutions, buffers, or other solutions, these components may be pre-mixed with the substrates (e.g., substrates containing surface-bound moieties or substrates lacking surface-bound moieties) of the kit, or they may be separately contained within the kit.

The kits provided herein may further contain additional components (e.g., reagents) for use in visualizing or otherwise ascertaining the presence or absence of antibodies bound to the surface-bound moieties upon or after contacting a biological sample. This can include anti-human globulin or other material that induces agglutination, as well as any other components useful in visualization methods such as IAT or DAT. In certain embodiments, the kits provided herein may contain materials suitable for use as controls (e.g., standards).

Also provided are systems comprising the aforementioned kits, as would be readily appreciated by one skilled in the art. For example, the system further includes automatic equipment that can be used in accordance with the methods described herein.

Methods of Preparation

Provided herein are methods for preparing a panel of substrates (e.g., polymeric particles, RBCs). In some embodiments, the method comprises providing a first and a second sample each comprising a substrate; and treating the substrate of a first sample with a compound or derivative provided herein. In some embodiments, the method comprises providing a first and a second sample comprising polymeric particles (e.g., beads, microspheres); and treating the polymeric particles of a first sample with a compound or derivative provided herein. In some embodiments, the method comprises providing a first and a second sample comprising RBCs; and treating the RBCs of a first sample with a compound or derivative provided herein. In some embodiments, the RBCs of the first and second samples are obtained from the same blood donor. The treatment step may further include additional reagents, such as an acid, a base, a suitable catalyst, or any other reagent that may facilitate reaction of the compound or derivative with the substrate. Suitable solvents (e.g., water) or buffers (e.g., RBC additive solutions, blood bank saline) may be employed in the treatment step. The treatment step may result in covalent or non-covalent binding of a moiety to the surface of substrate (e.g., polymeric particles, RBCs) of the first sample. In some embodiments, the resultant surface-bound moiety has the same or substantially the same chemical structure as the compound or derivative used to treat the substrate (e.g., polymeric particles, RBCs) of the first sample. In some embodiments, the resultant surface-bound moiety has a substantially different chemical structure than the compound or derivative used to treat the substrate (e.g., polymeric particles, RBCs) of the first sample. For instance, the resultant surface-bound moiety may be a type of hydrolysis product of the reaction. Since the second sample is not treated with the compound, together with the first sample it produces a panel including the first sample of substrate (e.g., polymeric particles, RBCs) with a surface-bound moiety and the second sample of substrate (e.g., polymeric particles, RBCs) that lack the surface-bound moiety.

In some embodiments, the method for preparing a panel of substrates (e.g., polymeric particles, RBCs) can further include one or more steps of reacting the first and second sample with one or more additional antigens, such as one or more antigens commonly found in a biological sample (e.g., whole blood, red blood cells, serum, or plasma). The reaction with one or more additional antigens can occur prior to, concurrently with, or subsequent to the treatment with the compound or derivative. Solvents and additional reagents may be used in the reaction with the one or more additional antigens as appropriate.

The method for preparing a panel of substrates (e.g., polymeric particles, RBCs) can further include one or more steps of washing the first and the second samples following the step of treating the substrate (e.g., polymeric particles, RBCs) with the compound or derivative. The method may also further include a quenching step to facilitate removal of excess free compound or derivative from the substrate treatment mixture. In some embodiments, the quencher may be glutathione. The quenching step may occur prior to, concurrently with, or subsequent to a washing step. In certain embodiments, the method further includes a step of suspending the first and second samples (e.g., polymeric particles, RBCs) in a buffered suspension medium. In certain embodiments, the method further includes a step of adding a cryopreservative to the first and second samples after washing.

In some embodiments, the second sample is treated similarly to or identically to the first sample, except that the compound or derivative is omitted from the treatment step. This may serve to harmonize the characteristics of the first and second samples such that the second sample provides a suitable control.

The method may further include treating a third sample comprising substrate (e.g., polymeric particles, RBCs) with the compound or derivative in the same manner as the treatment of the first sample, such that treatment with the compound or derivative leads to a lower level of the moiety bound to the surface of substrate (e.g., polymeric particles, RBCs) of the third sample relative to the level of the moiety bound to the surface of the substrate (e.g., polymeric particles, RBCs) of the first sample. Accordingly, a first level of the moiety is bound to the surface of the substrate (e.g., polymeric particles, RBCs) of the first sample, and the second level is less than the first level. in some embodiments, this may be achieved by treating the substrate (e.g., polymeric particles, RBCs) of the third sample with a different amount of the compound or derivative than the substrate (e.g., polymeric particles, RBCs) of the first sample. In some embodiments, this may alternatively be achieved by treating the substrate (e.g., polymeric particles, RBCs) of the third sample with the compound or derivative for a shorter length of time than the treatment of the RBCs of the first sample. In yet another alternative, the third sample is treated with a smaller amount of the compound or derivative than is used in treatment of the first sample, and the treatment is carried out on the third sample for a shorter length of time than the treatment of the first sample. Furthermore, any of the additional preparation steps described herein with respect to the first sample can be carried out as well on the third sample.

In some embodiments, the third sample is reacted with one or more additional antigens, such as one or more antigens commonly found in a biological sample (e.g., whole blood, red blood cells, or plasma). The reaction with one or more additional antigens can occur prior to, concurrently with, or subsequent to the treatment with the compound or derivative. Solvents and additional reagents may be used in the reaction with the one or more additional antigens as appropriate.

In some embodiments, the third sample is subjected to one or more steps of washing steps following the step of treating the substrate (e.g., polymeric particles, RBCs) with the compound or derivative. The method may also further include a quenching step to facilitate removal of excess free compound or derivative from the treatment mixture. The quenching step may occur prior to, concurrently with, or subsequent to a washing step. In certain embodiments, the method further includes a step of suspending the third sample (e.g., polymeric particles, RBCs) in a buffered suspension medium. In certain embodiments, the method further includes a step of adding a cryopreservative to the third sample after washing.

In some embodiments, the first, second, and third samples are treated identically, except that the amount of compound or derivative used in the treatment step is less for the third sample relative to the first sample, and the compound or derivative is omitted from the treatment step for the second sample.

The identity and loading level of the surface-bound moiety on the substrate may be assessed by any suitable method known in the art. Loading levels may be determined, for example, by labeling (e.g., radiolabeling, immunolabeling, chemical labeling, fluorescence labeling, chemiluminescence) a compound prior to adding to a substrate and then detecting the label after combining the compound with the substrate. Alternatively or in addition, loading level may be measured by directly or indirectly labeling (e.g., immunolabeling, immunofluorescence, chemiluminescence) a compound after adding to a substrate and then detecting the label. Generally, such labeling is performed separately (e.g., as control, as standard curve) from the compound used in the kits and methods provided herein, as a comparator or point of reference in determining the absolute loading levels or relative loading levels. Such labeling may be directly quantitated using a quantitative or semi-quantitative method, or may be compared to a reference standard, such as for example cells, beads or other materials with a known amount of similarly labeled molecule on the surface (e.g., FACS analysis). A substrate may be monitored for the presence of at least a certain level of a particular resultant surface-bound moiety. A substrate may be monitored for the presence of at least a certain loading level of all resultant surface-bound moieties.

The first, second, and optional third samples may be sterilized according to any method known in the art. The sterilization may occur prior to or subsequent to the treatment with the compound or derivative.

A panel of substrates (e.g., polymeric particles, RBCs) including a first, second, and optional third sample can be packed for storage. Any suitable storage container (e.g., box, bag, jar, tube) known in the art may be used. In some embodiments, the storage container is sterile. In some embodiments, freezing is required. For example, when the substrate-bound moiety contains a hydrolysable linker as describe above, samples in the panel may be frozen for storage. In other embodiments, samples in a panel may not be frozen.

Methods of Use

Provided herein are methods for testing a biological sample using a kit described herein. In various embodiments, a substrate in a kit described herein comprises polymeric particles, a matrix, a portion of an assay plate, or cells, such as for example, RBCs.

Methods of Testing a Sample

Provided herein is a method of testing a sample for the presence of an antibody that binds a compound, the method comprising: a) providing a sample comprising serum or plasma; b) contacting the sample with a substrate, wherein a moiety is bound to the surface of the substrate; and wherein the moiety is selected from the group consisting of compounds of any of Formulae I, II, III, IV, IV(a)-IV(h), V, VI, VII, VIII, and IX, and derivatives thereof, or a salt or stereoisomer of any of the foregoing; c) assaying an amount of binding between antibody from the sample and the surface-bound moiety of the substrate, wherein binding between the antibody and the surface-bound moiety indicates that the antibody binds the compound.

In some embodiments, the method of testing a sample for the presence of an antibody that binds a compound comprises: a) providing a sample comprising serum or plasma; b) contacting the sample with a polymeric particle (e.g., bead, microsphere), matrix or portion of an assay plate, wherein a moiety is bound to the surface of the polymeric particle (e.g., bead, microsphere), matrix or portion of an assay plate; and wherein the moiety is selected from the group consisting of compounds of any of Formulae I, II, III, IV, IV(a)-IV(h), V, VI, VII, VIII, and IX, and derivatives thereof, or a salt or stereoisomer of any of the foregoing; c) assaying an amount of binding between antibody from the sample and the surface-bound moiety of the polymeric particle (e.g., bead, microsphere), matrix or portion of an assay plate, wherein binding between the antibody and the surface-bound moiety indicates that the antibody binds the compound.

In some embodiments, the method of testing a sample for the presence of an antibody that binds a compound comprises: a) providing a sample comprising serum or plasma; b) contacting the sample with red blood cells, wherein a moiety is bound to the surface of the red blood cells; and wherein the moiety is selected from the group consisting of compounds of any of Formulae I, II, III, IV(a)-IV(h), VII, VIII, and IX, and derivatives thereof, or a salt or stereoisomer of any of the foregoing; c) assaying an amount of binding between antibody from the sample and the surface-bound moiety of the red blood cells, wherein binding between the antibody and the surface-bound moiety indicates that the antibody binds the compound.

Provided herein is a method for testing a sample for the presence of an antibody that binds a compound. In some embodiments, the method comprises providing a sample comprising serum or plasma, and contacting the sample with a substrate (e.g., RBCs), wherein a moiety is bound to the surface of the substrate, which is followed by assaying an amount of binding between antibody from the sample and the surface-bound moiety of the substrate.

In some embodiments, the step of assaying includes comparing the amount of binding between antibody from the sample and the surface-bound moiety with a reference, wherein an increased amount of binding as compared with the reference indicates the presence of the antibody in the sample. In some embodiments, the reference is the same substrate as the substrate having the surface-bound moiety, except that the surface-bound moiety is absent.

In some embodiments, the step of assaying includes assaying an amount of binding between the antibody from the sample and a substrate (e.g., RBCs) that lack the surface-bound moiety. The method may further include assaying an amount of binding between antibody from the sample and a substrate (e.g. RBCs) having a lesser amount of the surface-bound moiety, as compared with the sample.

In some embodiments, the step of assaying an amount of binding between the antibody from the sample and the substrate (e.g., RBCs) includes contacting the substrate to which the sample has been added with anti-human globulin, and the assay step includes assaying for an amount of agglutination. Conventional methods for measurements such as solid-phase red cell adherence assay (e.g., Galileo System, Immucor) or IAT and DAT can be used (e.g., gel card, ID-Card DiaScreen gel card, Bio-Rad).

In some embodiments, a testing method provided herein is used to determine whether a subject is expected to have an immune response to a pathogen-inactivated red blood cell infusion. Exemplary pathogen-inactivated red blood cell compositions that can be used for infusion into a subject are described in U.S. Pat. No. 6,270,952, US 2003/0113704, U.S. Pat. No. 7,655,392, and WO 2009/126786, the contents of each of which is hereby incorporated by reference. In some embodiments, the surface-bound moiety on the substrate used in the method is the same as the pathogen-inactivating compound used to treat the red blood cells for infusion or a derivative of such pathogen-inactivating compound. In other embodiments, the surface-bound antigen on the substrate used in the method is an analog of the pathogen-inactivating compound used to treat the red blood cells for infusion or a derivative of such analog. For instance, if the pathogen-inactivating compound used to treat the red blood cells for infusion is a frangible compound (e.g., S-303), a non-frangible analog of the pathogen-inactivating compound may be used as the surface-bound moiety on the substrate. The non-frangible analog may exhibit a similar epitope for antibody binding as the pathogen-inactivating compound and may exhibit a similar binding affinity to the antibody as does the pathogen-inactivating compound itself. An advantage of using a non-frangible analog as the surface-bound moiety may be that the substrate containing the non-frangible surface-bound moiety may be more stable than a substrate containing a frangible surface-bound moiety. A substrate containing a non-frangible surface-bound moiety may thus be amenable to storage at room temperature or refrigeration temperature, whereas the substrate containing the corresponding frangible surface-bound moiety may require freezer storage in order to avoid degradation of the surface-bound moiety (e.g. via hydrolysis of the frangible linker).

In some embodiments, the sample is from a subject in need of an infusion of red blood cells. For instance, the sample may be a serum sample, a plasma sample, or other blood sample from a subject in need of an infusion of red blood cells. In some embodiments, the method of testing a sample provided herein includes a first step of obtaining a sample from a subject. The sample may be obtained from the subject by any method known in the art, such as by a standard blood draw from the arm or finger.

The method may be carried out using any of the compositions or kits provided herein. Where the composition or kit is stored in a freezer, the composition or kit is removed from the freezer and thawed prior to contacting the substrate (e.g. red blood cells) of the kit or composition with the sample. The kit may be thawed in the refrigerator or at room temperature.

Method of Providing a Blood Transfusion

Provided herein is a method of providing a blood transfusion to a subject in need thereof, wherein the blood transfusion includes RBCs treated with a pathogen-inactivating compound (e.g., a pathogen-inactivating compound described herein). The method includes providing a sample from the subject (e.g., a serum sample or plasma sample); contacting the sample with a substrate (e.g., polymeric particles, RBCs), wherein a moiety is bound to the surface of the substrate, assaying an amount of binding between an antibody from the sample and the surface-bound moiety of the sample as compared to a reference, determining whether the amount of binding between the antibody and the surface-bound moiety is higher than the reference; and, in accordance with a determination that the amount of binding is not higher than the reference, providing an infusion of pathogen-inactivated red blood cells to the subject. The surface-bound moiety may be the same as the pathogen-inactivating compound used to treat the red blood cells for infusion. Alternatively, the surface-bound moiety may be a derivative (e.g., hydrolyzed derivative) of the pathogen-inactivating compound used to treat the red blood cells for infusion. In yet another alternative, the surface-bound moiety may be an analog of the pathogen-inactivating compound used to treat the red blood cells for infusion. For example, if the pathogen-inactivating compound used to treat the red blood cells for infusion contains a frangible linker (e.g., S-303), the surface-bound moiety may be a non-frangible analog thereof or a derivative of such non-frangible analog.

In some aspects, the method includes providing a sample from the subject (e.g., a serum sample or plasma sample); contacting the sample with a substrate (e.g., polymeric particles, RBCs), wherein a moiety is bound to the surface of the substrate, assaying an amount of binding between an antibody from the sample and the surface-bound moiety of the sample as compared to a reference, determining whether the amount of binding between the antibody and the surface-bound moiety is higher than the reference; and, in accordance with a determination that the amount of binding is higher than the reference, providing an infusion of red blood cells that have not been pathogen-inactivated to the subject. The surface-bound moiety may be the same as the pathogen-inactivating compound used to treat the red blood cells for infusion. Alternatively, the surface-bound moiety may be a derivative (e.g., hydrolyzed derivative) of the pathogen-inactivating compound used to treat the red blood cells for infusion. In yet another alternative, the surface-bound moiety may be an analog of the pathogen-inactivating compound used to treat the red blood cells for infusion. For example, if the pathogen-inactivating compound used to treat the red blood cells for infusion contains a frangible linker (e.g., S-303), the surface-bound moiety may be a non-frangible analog thereof or a derivative of such non-frangible analog.

In some embodiments, the method comprises providing a sample comprising serum or plasma, and contacting the sample with a substrate (e.g., polymeric particles, RBCs), wherein a moiety is bound to the surface of the substrate, which is followed by assaying an amount of binding between antibody from the sample and the surface-bound moiety of the substrate.

In some embodiments, the step of assaying includes comparing the amount of binding between antibody from the sample and the surface-bound moiety with a reference, wherein an increased amount of binding as compared with the reference indicates the presence of the antibody in the sample. In some embodiments, the reference is the same substrate as the substrate having the surface-bound moiety, except that the surface-bound moiety is absent.

In some embodiments, the step of assaying includes assaying an amount of binding between the antibody from the sample and a substrate (e.g., polymeric particles, RBCs) that lack the surface-bound moiety. The method may further include assaying an amount of binding between antibody from the sample and a substrate (e.g. polymeric particles, RBCs) having a lesser amount of the surface-bound moiety, as compared with the sample.

In some embodiments, the step of assaying an amount of binding between the antibody from the sample and the substrate (e.g., polymeric particles, RBCs) includes contacting the substrate to which the sample has been added with anti-human globulin, and the assay step includes assaying for an amount of agglutination. Conventional methods for measurements such as IAT and DAT can be used.

In some embodiments, the determination that the amount of binding of the antibody to the surface-bound moiety of the substrate is not higher than a reference is made using substrate lacking the surface-bound moiety as a reference. In some embodiments, the determination that the amount of binding of the antibody to the surface-bound moiety of the substrate is not higher than a reference is made using substrate having a lower loading level of the surface-bound moiety as a reference. It may be advantageous to have the reference substrate differ from the test substrate only in the presence or absence of the surface-bound moiety or with respect to the loading level of the surface-bound moiety.

The sample from the subject may be collected and tested for antibody binding to a surface-bound moiety immediately before the intended infusion of red blood cells or within 5 minutes, 10 minutes, 30 minutes, 1 hour, 2 hours, 4 hours, 12 hours, or 24 hours, 48 hours, 72 hours, 1 week, 2, weeks, 3 weeks, 4 weeks, or 5 weeks or longer prior to the intended infusion of red blood cells. If a subject is to receive more than one infusion of red blood cells over a period of time, a sample from the subject may be tested according to the methods described herein prior to each infusion of red blood cells (e.g., pathogen-inactivated red blood cells), or prior to only the first infusion of red blood cells (e.g., pathogen-inactivated red blood cells), or on a periodic basis as determined by a medical professional.

EXAMPLES

The invention is further illustrated by the following non-limiting examples.

Example 1: Preparation of Red Blood Cell Panels

Red Blood Cell Panel with S-303

S-303 treated and control reagent RBCs were prepared to include 1) control RBCs with no bound adducts from S-303, 2) RBCs treated with S-303 and glutathione (GSH) quencher under conditions to generate high levels of bound adducts from S-303, and 3) RBCs treated with S-303 and glutathione (GSH) quencher under conditions to generate low levels of bound adducts from S-303. More specifically, RBC units were obtained from human donors by standard blood collection techniques, and each RBC unit was split into three matched smaller (sub-) unit samples of 100 mL that were then used to prepare the reagent cell panel under three different treatment conditions. To generate high levels of bound adducts, one of the three matched RBC units was mixed in a processing solution (see e.g., U.S. Pat. Nos. 7,655,392 and 8,900,805) with about 0.2 mM S-303 and about 2 mM GSH, incubated overnight at room temperature, and washed with 0.9% NaCl prior to freezing at −80° C. in Glycerolyte. To generate low levels of bound adducts, one of the three matched RBC units was mixed in processing solution with about 0.2 mM S-303 and about 20 mM GSH, incubated overnight at room temperature, and washed with 0.9% NaCl prior to freezing at −80° C. in Glycerolyte. The control RBC were not subjected to S-303/GSH treatment, but washed with 0.9% NaCl prior to freezing at −80° C. in Glycerolyte.

The reagent panel was evaluated to determine if the RBC reagents with higher levels of surface adducts provide greater sensitivity in antibody detection compared to the RBC reagents with lower levels of surface adducts. For this evaluation, a previously characterized monoclonal antibody against the acridine moiety of S-303 (generated from immunizing mice with KLH-conjugated S-197, a non-frangible analog of S-303) was titrated and the various mAb dilutions used in a gel card assay (e.g., ID-MTS™ Ortho Diagnostics, Raritan, NJ). The anti-acridine S-197 mAb titration tested against the low S-303 adduct RBC resulted in a median titer (inverse of the highest dilution) of 8,000. In contrast, anti-acridine S-197 mAb dilutions tested against high S-303 adduct RBCs resulted in a median titer of 32,000. These data indicate that the high adduct RBC provide greater detection of antibody against the acridine moiety of S-303 RBCs.

Binding Stability of a Non-Frangible Analog Compound

A study was performed to assess binding to RBC substrate by the compound 5-220, which is a non-frangible analog of S-303. This study also compared the stability of the surface bound moiety of the 5-220 compound to the stability of a similarly bound frangible S-303. More specifically, glutathione (GSH) quencher and the 5-220 compound were added to human RBC's substrate at concentrations of 2.0 mM and 0.2 mM, respectively, and then incubated overnight at 37° C. or 4° C. For comparison, GSH quencher and the frangible S-303 compound were similarly added to human RBC's at concentrations of 2.0 mM and 0.2 mM, respectively, and incubated overnight at 37° C. or 4° C. Both the non-frangible 5-220 and frangible S-303 compounds comprise an acridine moiety as part of their structures. Following incubation, the GSH/S-220 and GSH/S-303 treated RBC's were stained with either a mouse monoclonal (mAb) or rabbit polyclonal (polyAb) anti-acridine antibody (also at 4° C. or 37° C.), and the samples analyzed for antibody binding by flow cytometry using standard methods (quantitated as MFI). Both the mAb and polyAb anti-acridine antibodies were generated using the compound 5-197 for immunization.

Figure 2:
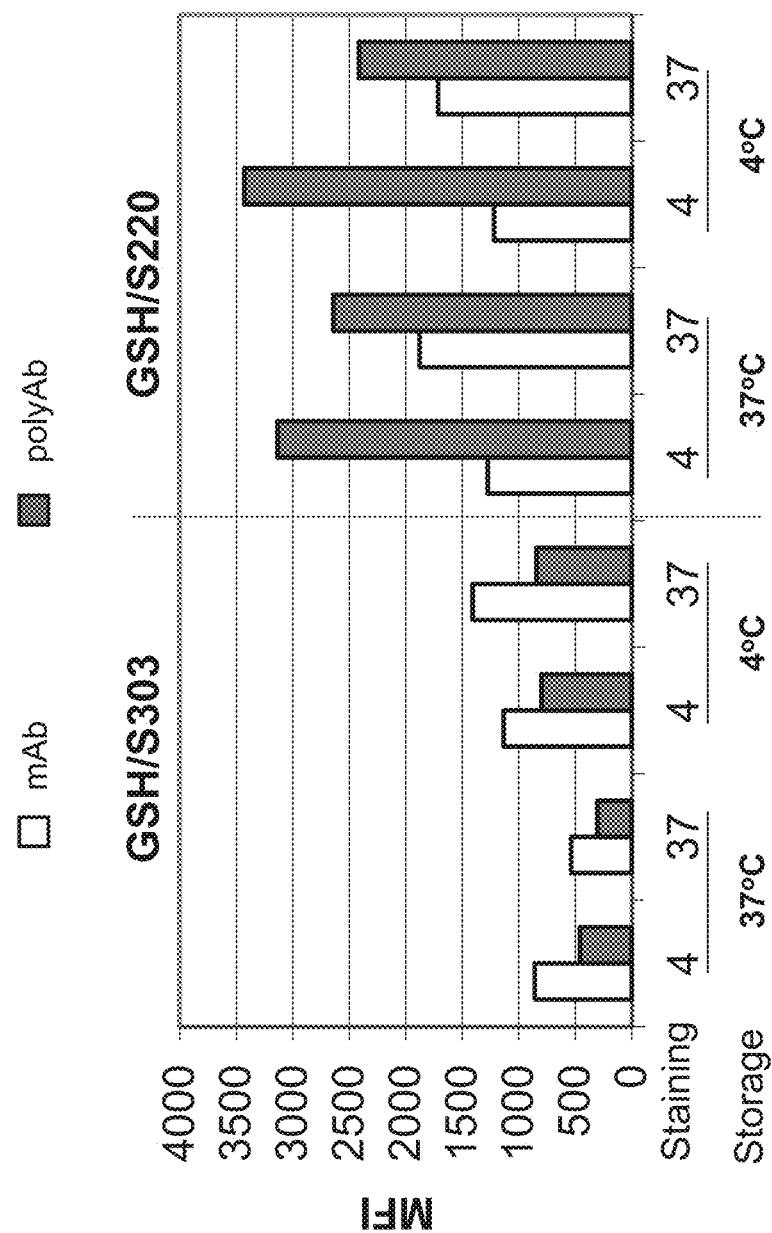
FIG. 2 is a graph showing levels of antibody staining of treated red blood cells.
Figure 3:
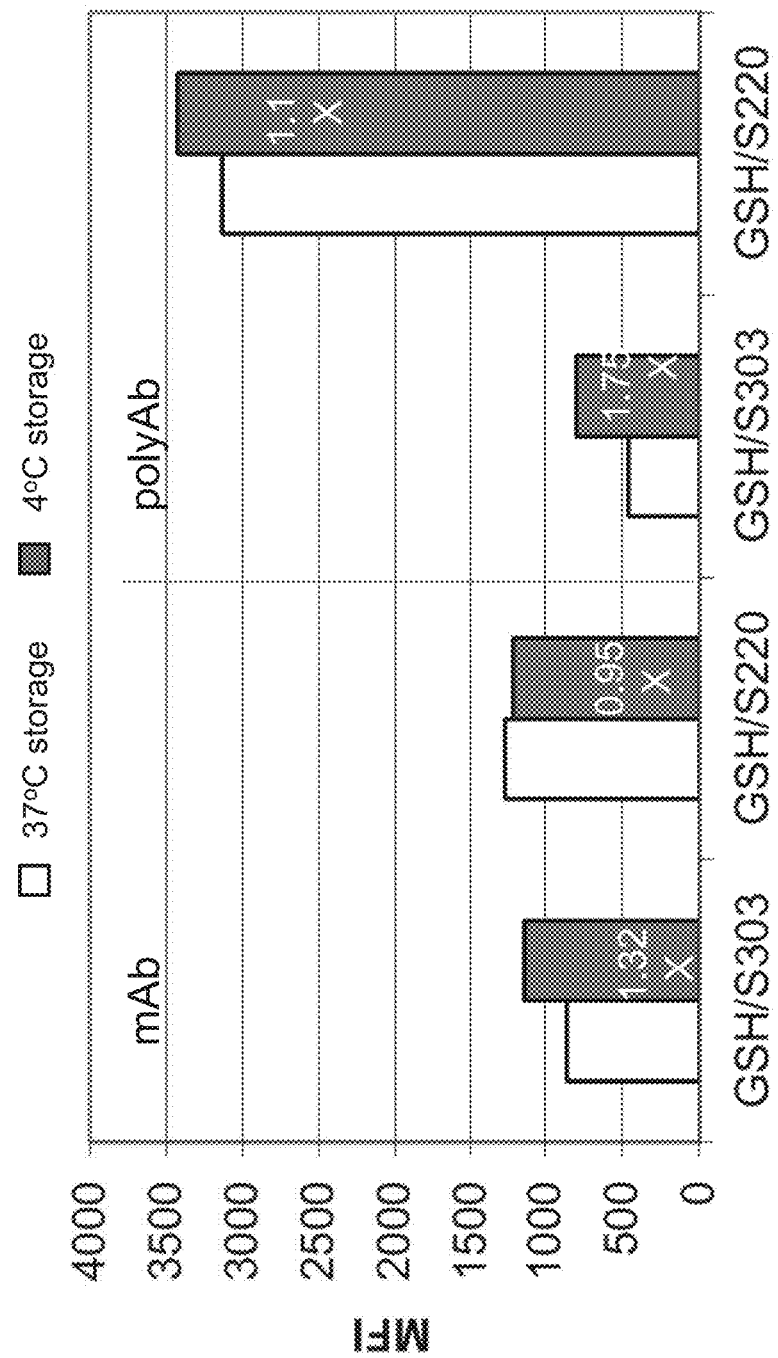
FIG. 3 is a graph showing levels of antibody staining of treated red blood cells.
Figure 4:
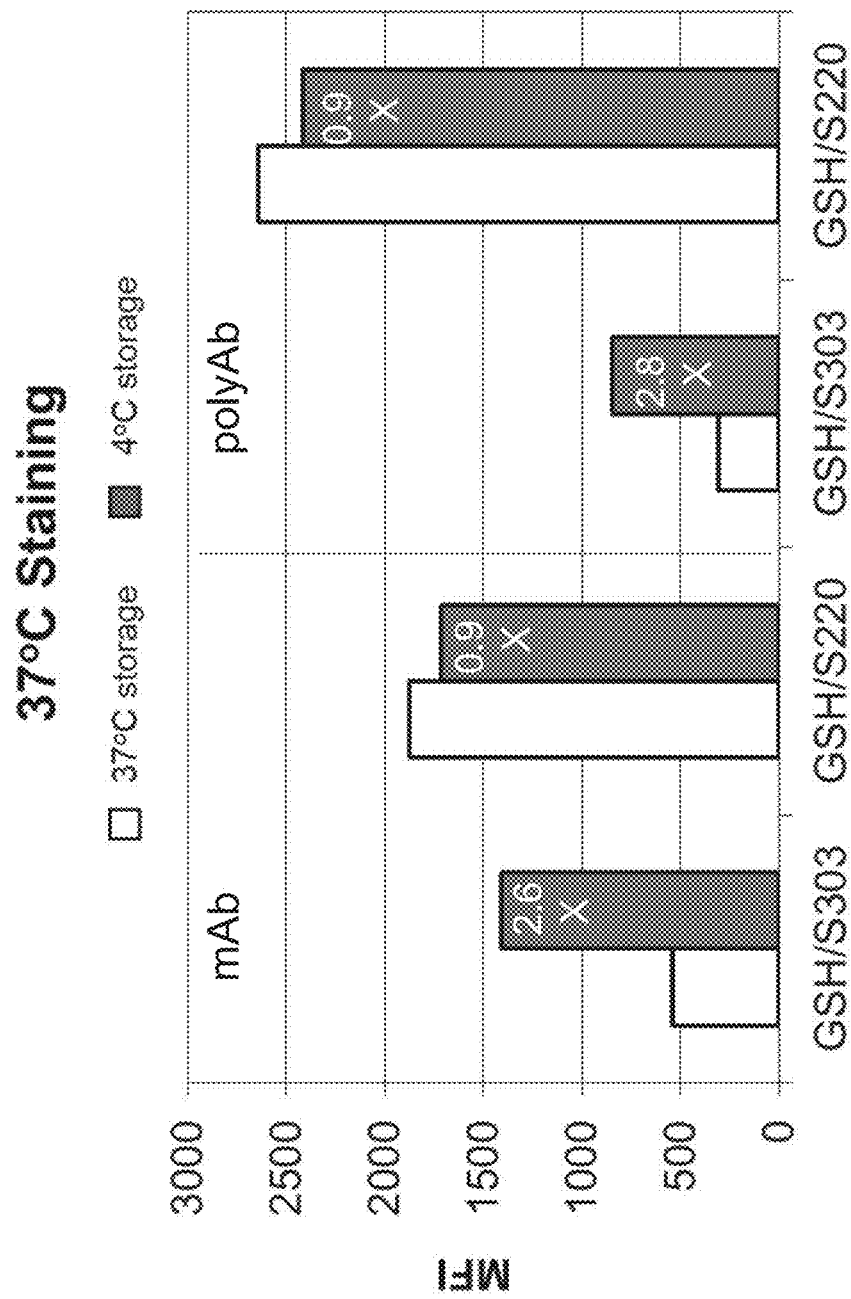
FIG. 4 is a graph showing levels of antibody staining of treated red blood cells.
Figure 5:
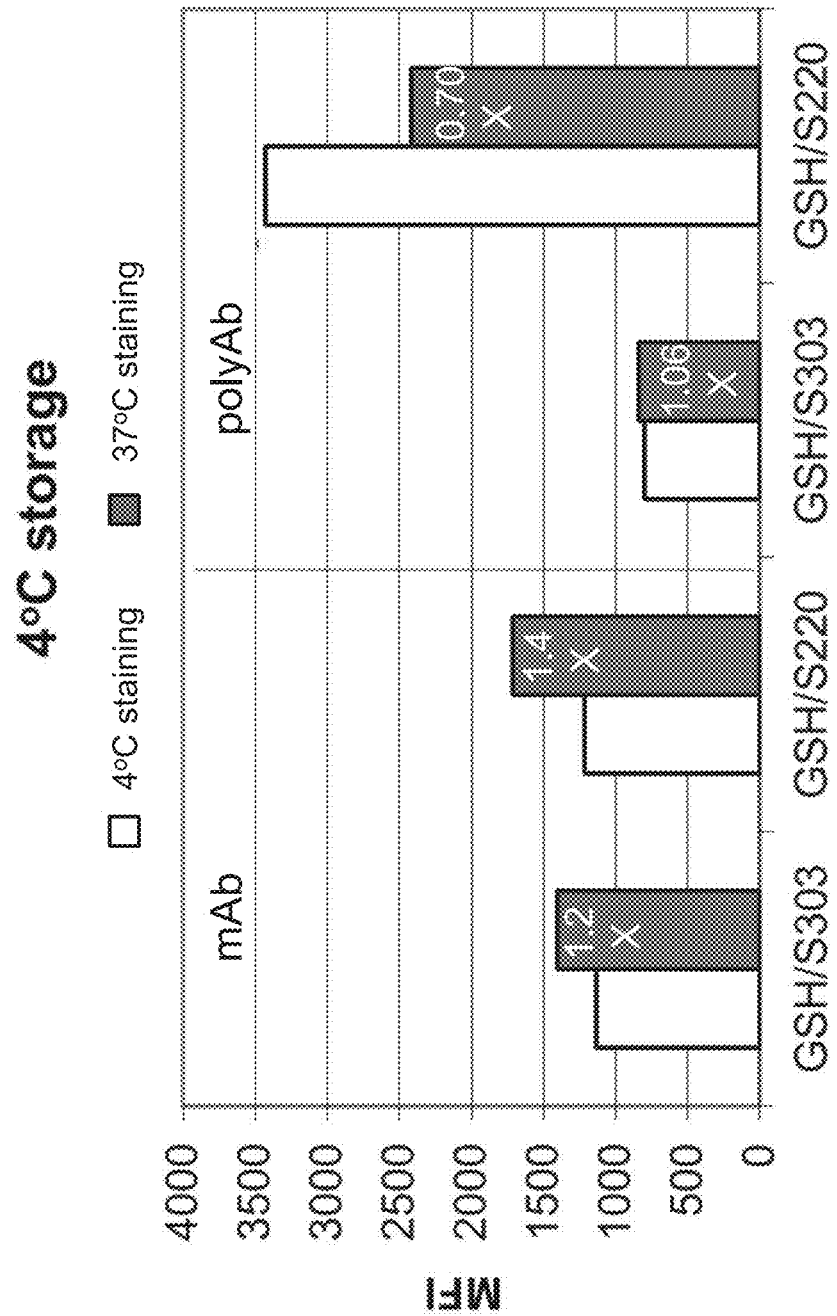
FIG. 5 is a graph showing levels of antibody staining of treated red blood cells.

As shown in FIGS. 1-6, both the non-frangible 5-220 and frangible S-303 treated RBCs can achieve similar levels of binding. Additionally, while some differences were observed between the monoclonal and polyclonal antibody binding of the treated RBCs, data with both antibodies indicate that S-303 binding to RBC's is less stable than 5-220 binding to RBC's at 37° C., suggesting a benefit to using non-frangible compounds in the methods and kits provided herein.

Red Blood Cell Panels

Red blood cells (RBCs) are obtained from group O donors by standard blood collection techniques. The cells express one or more of the antigens C, c, E, e, K, k, Fya, Fyb, Jka, Jkb, M, N, S, s, P1, Lea, and Leb. Each unit of RBCs (approx. 350 mL) is split into 3 matched smaller units (e.g., subunits) of approximately equal volume (designated subunits A, B, and C). Subunit A is treated with a non-frangible analog of S-303 (e.g., S-220, S-197) and 2 mM glutathione, followed by washing in 0.9% NaCl, to produce a "high"

level of surface-bound adducts. Subunit B from the same donor unit is treated with the same non-frangible analog of S-303 and 20 mM glutathione, followed by washing in 0.9% NaCl, to produce a "low" level of surface-bound adducts. By varying the non-frangible analog and/or glutathione concentration, other levels of surface-bound adducts may be achieved. Subunit C is not treated with the non-frangible analog of S-303 or glutathione. Subunit C is washed in 0.9% NaCl. Following the treatment steps described herein, each of the subunits is suspended in a buffered suspension medium (e.g., at 3% RBCs) and transferred to one or more storage containers. Optionally, Glycerolite is added to each of subunits A, B, and C, and the subunits are then stored at −80° C. Subunits A, B, and C form a Primary Panel.

A Secondary Panel is prepared analogously to the Primary Panel, except that the RBCs of subunits A, B, and C are each from a different group O donor.

Example 2: Testing of Patient Serum Sample

One, two, or three Primary Panels of Example 1 are thawed to room temperature. Each Primary Panel contains subunits A, B, and C from a single group O donor. Serum from a patient and anti-human globulin is added to each of subunits A, B, and C of each of the Primary Panels. The subunits of each Primary Panel are monitored for agglutination and assigned a score of 0, 1, 2, or 3, where 0 represents no agglutination, and 1, 2, and 3 represent progressively larger amounts of agglutination.

If the antibody score is 0 (i.e., no agglutination observed) for subunits A, B, and C, of each of the Primary Panels, the sample is considered "non-reactive," and the patient may be administered an infusion of RBCs that have been treated with S-303 as a pathogen-inactivating compound.

If the antibody score is ≥1 is observed with any of the RBCs in the Primary Panels, the patient sample undergoes additional testing with a Secondary Panel, as described in Example 1. If the score on all three Primary Panels is ≥ for either the "high" or "low" levels of surface-bound adducts (i.e., subunit A or subunit B), and the score is 0 with the corresponding untreated control RBCs (i.e., subunit C), the sample is classified as "initial reactive." If the Secondary Panel score shows the same reactivity pattern as any of the Primary Panels, the sample is classified as "confirmed reactive." The patient is given infusions of RBCs as needed which have not been treated with S-303.

If the antibody score is ≥1 for either the "high" or "low" levels of surface-bound adducts (i.e., subunit A or subunit B) on one or two but not all three of the Primary Panels, and the corresponding untreated reagent control RBCs show a score of 0 on all of the Primary Panels, the sample is classified as "indeterminate reactive." If the Secondary Panel results show no agglutination from the RBCs with surface-bound adducts, then the sample is classified as "non-reactive," and the patient may be administered an infusion of RBCs that have been treated with S-303 as a pathogen-inactivating compound.

If the results of the three Primary Panels show three of three, two of three, or one of three reactivity with both the RBCs with surface-bound adducts and the corresponding control untreated RBCs, the sample will be considered to have a "presumed allo-reactive" antibody to an intrinsic red cell antigen.

What is claimed is:

1. A method of administering a red blood cell transfusion to a patient, wherein the red blood cell transfusion comprises red blood cells treated with a pathogen-inactivating compound β-alanine, N-(acridin-9-yl), 2-[bis(2-chloroethyl)amino]ethyl ester (S-303-treated RBCs), the method comprising:

a) testing a sample from the patient for presence of antibodies reactive to the S-303-treated RBCs according to a method comprising:
      i) providing the sample from the patient, wherein the sample comprises serum or plasma;
      ii) contacting the sample with a first substrate, wherein a moiety is bound to the surface of the first substrate, and wherein the surface-bound moiety resulted from treating the first substrate with a compound of Formula VIII:

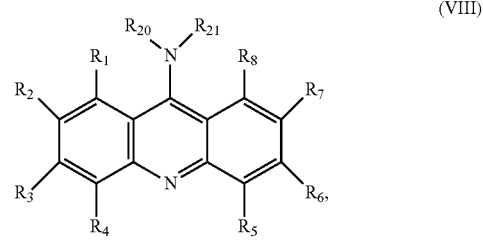

(VIII)

where $R_1$, $R_2$, $R_3$, $R_4$, $R_5$, $R_6$, $R_7$, and $R_8$ are each —H; $R_{20}$ is —H; and $R_{21}$ is —$R_{11}$—X-E, where —$R_{11}$— is unsubstituted-$C_{1-8}$alkyl-; X is independently —$R_{11}$—; and E is $N(R_{12})_2$; where —$R_{12}$ is —$CH_2CH_2$-G, and where each G is independently —Cl, —Br, or —I, or a salt or stereoisomer thereof;

iii) assaying an amount of binding between antibodies from the sample and the surface-bound moiety of the first substrate as compared to a reference, wherein the binding between the antibodies and the surface-bound moiety indicates the presence of antibodies in the sample that are reactive to the S-303-treated RBCs, wherein the reference is a second substrate that lacks the surface-bound moiety, and the second substrate is the same as the first substrate;

b) determining whether the amount of binding is higher than the reference; and c) administering the red blood cell transfusion to the patient in accordance with the determination that the amount of binding is not higher than the reference.

2. The method of claim 1, wherein $R_{21}$ is —$C_{1-8}$alkyl-N($CH_2CH_2Cl)_2$.

3. The method of claim 1, wherein the surface-bound moiety resulted from treating the first substrate with S-197:

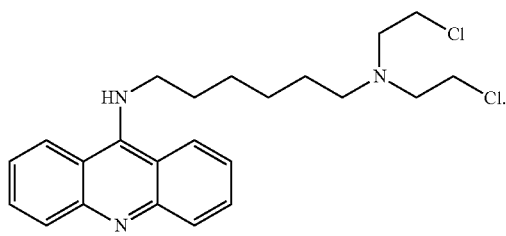 [SMILES: ClCCN(CCCl)CCCCCCNc1c2ccccc2nc2ccccc12]

4. The method of claim 1, wherein the surface-bound moiety resulted from treating the first substrate with S-220:

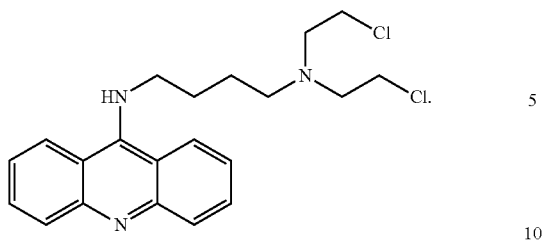

5. The method of claim 1, wherein the moiety bound to the surface of the first substrate is present at a loading level of at least about 10,000 moieties per red blood cell.

6. The method of claim 1, wherein the moiety bound to the surface of the first substrate is present at a loading level of at least about 50 moieties/μm$^2$.

7. The method of claim 1, wherein the substrate comprises a polymeric particle, matrix, or portion of an assay plate.

8. The method of claim 1, wherein the substrate comprises red blood cells.

9. The method of claim 1, wherein step (ii) comprises contacting the sample and the substrate with anti-human globulin, and wherein step (iii) comprises assaying an amount of agglutination.

10. The method of claim 1, wherein step (iii) further comprises assaying an amount of binding between antibodies from the sample and a third substrate having a reduced amount of the surface-bound moiety as compared with the first substrate.

* * * * *